United States Patent
Wyman et al.

(10) Patent No.: US 10,751,435 B2
(45) Date of Patent: Aug. 25, 2020

(54) SANITATION COMPLIANCE

(71) Applicants: Steven N. Wyman, Boise, ID (US);
Robert T. Wyman, Santa Barbara, CA (US); Joseph L. Acayan, Soquel, CA (US)

(72) Inventors: Steven N. Wyman, Boise, ID (US);
Robert T. Wyman, Santa Barbara, CA (US); Joseph L. Acayan, Soquel, CA (US)

( * ) Notice: Subject to any disclaimer, the term of this patent is extended or adjusted under 35 U.S.C. 154(b) by 0 days.

(21) Appl. No.: 16/403,593

(22) Filed: May 5, 2019

(65) Prior Publication Data
US 2019/0255206 A1 Aug. 22, 2019

Related U.S. Application Data

(63) Continuation of application No. 15/382,617, filed on Dec. 17, 2016, now Pat. No. 10,279,061.

(60) Provisional application No. 62/269,982, filed on Dec. 19, 2015.

(51) Int. Cl.
| A61L 2/24 | (2006.01) |
| A47K 5/12 | (2006.01) |
| A61L 2/00 | (2006.01) |
| A61L 2/18 | (2006.01) |
| A61L 2/04 | (2006.01) |
| A61L 2/06 | (2006.01) |
| A61L 2/10 | (2006.01) |
| E05B 1/00 | (2006.01) |

(52) U.S. Cl.
CPC .............. *A61L 2/24* (2013.01); *A47K 5/1217* (2013.01); *A61L 2/0088* (2013.01); *A61L 2/04* (2013.01); *A61L 2/06* (2013.01); *A61L 2/10* (2013.01); *A61L 2/18* (2013.01); *E05B 1/0069* (2013.01); *A61L 2202/11* (2013.01); *A61L 2202/14* (2013.01); *A61L 2202/15* (2013.01)

(58) Field of Classification Search
CPC ... A61L 2/24; A61L 2/10; A61L 2/085; A61L 2202/20
USPC .............................. 422/28, 292; 134/22.1, 42
See application file for complete search history.

(56) References Cited

U.S. PATENT DOCUMENTS

| 7,989,779 B1 * | 8/2011 | Ray | A61L 2/10 250/455.11 |
| 2006/0245818 A1 * | 11/2006 | Stropkay | A47K 5/12 401/207 |

* cited by examiner

*Primary Examiner* — Monzer R Chorbaji
(74) *Attorney, Agent, or Firm* — Joseph L. Acayan

(57) ABSTRACT

Implementations generally relate to a sanitizing platform. In one implementation, a system includes a base. The system also includes a first sanitizer mechanism coupled to the base, where the first sanitizer mechanism is configured to sanitize at least one hand of a user. The system also includes a second sanitizer mechanism coupled to the base, where the second sanitizer mechanism is configured to sanitize a door handle.

20 Claims, 14 Drawing Sheets

700

SANITATION COMPLIANCE

CROSS REFERENCE TO RELATED APPLICATIONS

This application claims priority from U.S. Provisional Patent Application No. 62/269,982, entitled "SANITATION PLATFORM," filed Dec. 19, 2015, and U.S. patent application Ser. No. 15/382,617, entitled "SANITATION PLATFORM," filed Dec. 17, 2016, which are hereby incorporated by reference as if set forth in full in this application for all purposes.

BACKGROUND

Patients in the hospital environment are impacted greatly by disease transmission through human or indirect contact. Infection control through hand cleaning is highly effective in combating this issue. Implementation in the modern hospital environment, however, leads to variable success.

SUMMARY

Implementations generally relate to a sanitizing platform. In one implementation, a system includes a base. The system also includes a first sanitizer mechanism coupled to the base, where the first sanitizer mechanism is configured to sanitize at least one hand of a user. The system also includes a second sanitizer mechanism coupled to the base, where the second sanitizer mechanism is configured to sanitize a door handle.

With further regard to the system, in some implementations, the first sanitizer mechanism sanitizes the at least one hand of the user by applying a hand sanitizer to the at least one hand of the user. In some implementations, the first sanitizer mechanism sanitizes the at least one hand of the user by applying a hand sanitizer to the at least one hand of the user, and where the hand sanitizer is a gel. In some implementations, the first sanitizer mechanism sanitizes the at least one hand of the user by applying a hand sanitizer to the at least one hand of the user, and where the hand sanitizer is a foam. In some implementations, the first sanitizer mechanism sanitizes includes a nozzle for applying a hand sanitizer to the at least one hand of the user. In some implementations, the second sanitizer mechanism sanitizes the door handle by applying a surface sanitizer to the door handle. In some implementations, the second sanitizer mechanism sanitizes the door handle by applying a surface sanitizer to the door handle, and where the surface sanitizer is light.

In some implementations, a system includes a base that mounts onto a door. The system also includes a door handle coupled to the base, where the door handle enables a user to operate the door. The system also includes a first sanitizer mechanism coupled to the base, where the first sanitizer mechanism is configured to sanitize at least one hand of the user. The system also includes a second sanitizer mechanism coupled to the base, where the second sanitizer mechanism is configured to sanitize the door handle.

With further regard to the system, in some implementations, the first sanitizer mechanism sanitizes the at least one hand of the user by applying a hand sanitizer to the at least one hand of the user. In some implementations, the first sanitizer mechanism sanitizes the at least one hand of the user by applying a hand sanitizer to the at least one hand of the user, and where the hand sanitizer is a gel. In some implementations, the first sanitizer mechanism sanitizes the at least one hand of the user by applying a hand sanitizer to the at least one hand of the user, and where the hand sanitizer is a foam. In some implementations, the first sanitizer mechanism sanitizes includes a nozzle for applying a hand sanitizer to the at least one hand of the user. In some implementations, the second sanitizer mechanism sanitizes the door handle by applying a surface sanitizer to the door handle. In some implementations, the second sanitizer mechanism sanitizes the door handle by applying a surface sanitizer to the door handle, and where the surface sanitizer is light.

In some implementations, a method includes detecting a hand of a user. The method further includes sanitizing the at least one hand of the user. The method further includes determining that the at least one hand of the user has released a door handle. The method further includes sanitizing the door handle.

With further regard to the method, in some implementations, the sanitizing of the at least one hand of the user includes applying a hand sanitizer to the at least one hand of the user using a first sanitizer mechanism. In some implementations, the first sanitizer mechanism sanitizes the at least one hand of the user by applying a hand sanitizer to the at least one hand of the user, and where the hand sanitizer is a gel. In some implementations, the first sanitizer mechanism sanitizes the at least one hand of the user by applying a hand sanitizer to the at least one hand of the user, and where the hand sanitizer is a foam. In some implementations, the determining that the at least one hand of the user has released a door handle includes no longer detecting the at least one hand of the user. In some implementations, the sanitizing of the door handle includes applying a surface sanitizer to the door handle using a second sanitizer mechanism.

DETAILED DESCRIPTION

Figure 1:
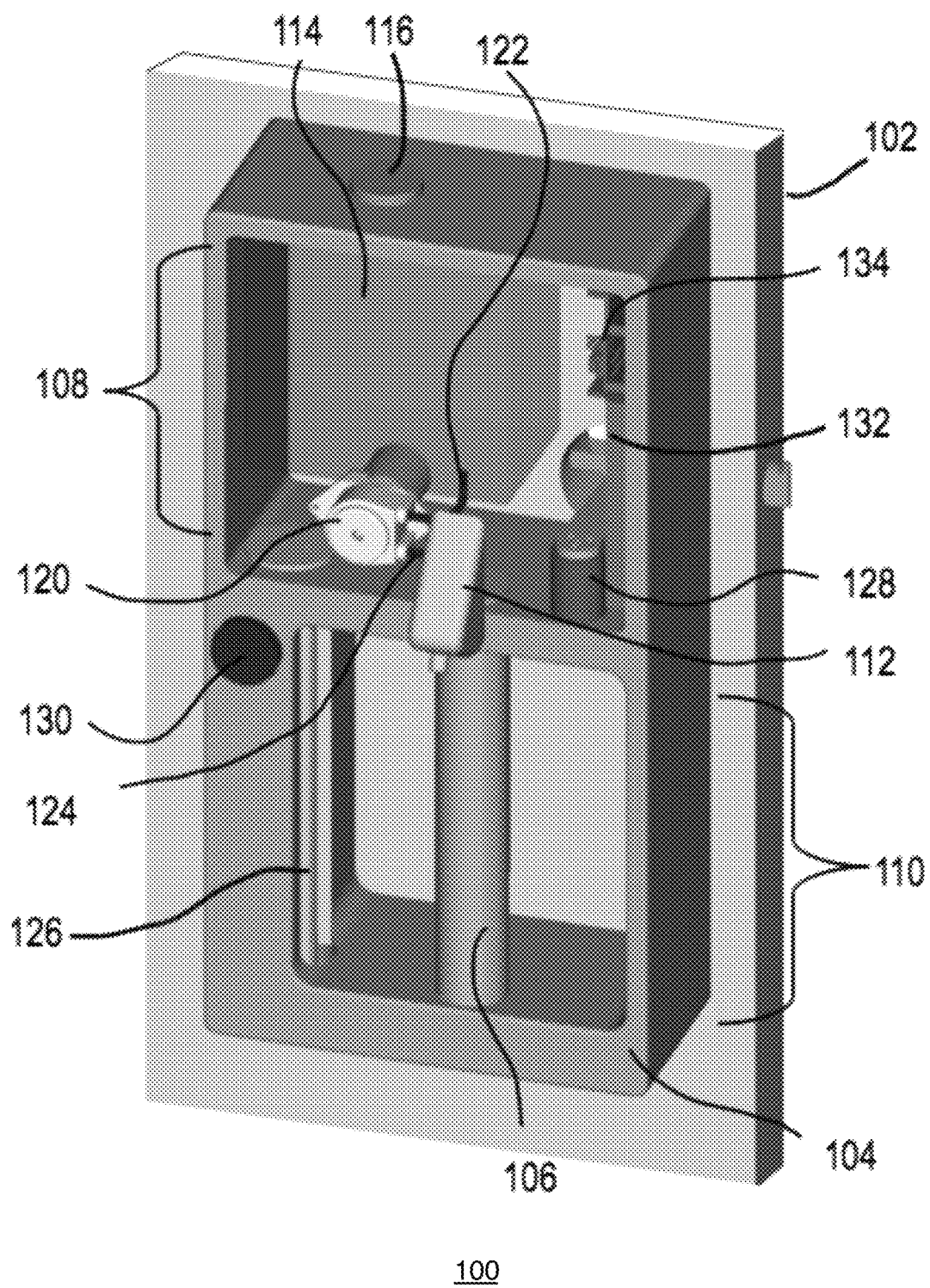
FIG. 1 illustrates a perspective view of a sanitation system, according to some implementations.

Implementations described herein provide, enable, facilitate, and manage entry point sanitation in a building such as a hospital. Implementations provide hand cleaning and door handle decontamination, as well as compliance with sanitation compliance procedures and requirements.

As described in more detail below, in various implementations, a system includes a hand sanitizer mechanism that is configured to sanitize the hands of a user. The system also includes a door handle sanitizer mechanism that is configured to sanitize a door handle. Multiple such systems may be deployed at different entry points of a building in order to comply with sanitation compliance procedures and requirements. In some implementations, an associated network compliance reporting system is provided.

Hand cleaning is typically performed in hospital environments with antibacterial soaps, foams or gels at dedicated stations throughout the facility. This task is dependent on personnel using them regularly or according to an established protocol. Compliance, however, is variable and dependent on individual behavior. The issue of surface borne contaminants that can be passed from one person to another or from one object to a person is difficult to manage. After a patient room is vacated, a list of decontamination activities may be followed to prepare a room, a zone, and equipment, and is not limited to these items. When a hospital room is cleared of patients and personnel it is not cleared of contamination that could spread virus or bacteria to others outside the room through casual contact.

Implementations described herein combat disease transmission in the hospital environment as specifically related to hand cleaning and for maintaining hand cleaning policy compliance for all personnel. Implementations advance a process that will become transparent to day-to-day activity. As personnel move between patients in the hospital environment they should be gated to clean hands in order to suppress cross contamination. The entrance to a patient's space is the typical locale for such a system. For this case, implementations combine the door entrance with hand cleaning. Each station acts as a node within a personnel tracking network. Tracking consists of identifying the person at an entry point, confirming hand cleaning and recording date/time.

Implementations described herein integrate the process of disinfecting hands, decontaminating the entry point door handle and maintaining hand cleaning compliance for each individual throughout the facility operation. The system and associated network involve methods to combat pathogen cross contamination in the hospital environment by providing efficient hand sanitation and effectuating hand cleaning compliance policies. As described in more detail below, implementations integrate personnel tracking, hand cleaning, and post use decontamination of and at the entry point of patient rooms in hospitals. Methods of tracking incorporate 2-way RFID tools. Likewise, hand cleaning uses chemicals that are used for hand sanitation. As described in more detail below, implementations integrate personnel tracking with the entry point system. Implementations may also apply a hand sanitizer to various portions of the hand. As described in more detail below, implementations also provide post use decontamination by employing several techniques.

FIG. 1 illustrates a perspective view of a sanitation system 100, according to some implementations. In various implementations, sanitation system 100 is configured as and may be referred to as a sanitation system assembly or an entry point assembly that is mounted at door entry points of different rooms in a building, such as a hospital. In some implementations, sanitation system 100 may be integrated into a door itself.

In various implementations, sanitation system 100 attaches to a door 102 (a partial door is shown). In various implementations, sanitation system 100 includes a base 104. In various implementations, base 104 of sanitation system 100 attaches or couples to door 102. In some implementations, sanitation system 100 includes a door handle 106, a first sanitizer mechanism 108 coupled to base 104, and a second sanitizer mechanism 110 also coupled to base 102. In various implementations, base 104 mounts onto a door, and door handle 106 enables a user to operate (e.g., open or close) the door.

In various implementations, first sanitizer mechanism 108 of sanitation system 100 is configured and operable to sanitize a hand of a user. First sanitizer mechanism 108 may also be referred to as hand sanitizer mechanism 108. In various implementations, hand sanitizer mechanism 108 sanitizes the hand of the user by applying a hand sanitizer to the hand of the user. As described in more detail below, various techniques may be used to apply a sanitizer to the hand of a user, and various types of sanitizers may be used.

In various implementations, second sanitizer mechanism 110 of sanitation system 100 is configured and operable to sanitize or disinfect door handle 106. Second sanitizer mechanism 110 may also be referred to as door handle sanitizer mechanism 110. In various implementations, door handle sanitizer mechanism 108 sanitizes door handle 106 by applying a surface sanitizer to door handle 106. As described in more detail below, various techniques may be used to apply a surface sanitizer to door handle 106. For example, in various implementations, the surface sanitizer is light. As described in more detail herein, the light may be ultraviolet light. In some implementations, the surface sanitizer is heat. In some implementations, the surface sanitizer may be a gel. In some implementations, the surface sanitizer may be a foam. In some implementations, the surface sanitizer may be a liquid. In some implementations, the surface sanitizer may be a gas. In some implementations, door handle sanitizer mechanism 110 may include a protective shield or sheath, where the sheath covers the door handle in order to prevent or block germs from the hand of the user from making direct contact with the door handle. In various implementations, the sheath may be made of paper, plastic, tape, and is not limited to these materials. The user may still grab and use the door handle while the sheath is over the door handle. In some implementations, during a door handle sanitation cycle, door handle sanitizer mechanism 110 moves the sheath away that has been in contact with the hand of the user from the door handle and replaces that sheath with paper that has not been in contact with the hand of the user. For example, in some implementations, the sheath may be continuous where a portion of the sheath covers the door handle. During the door handle sanitation cycle, the sheath door handle sanitizer mechanism 110 moves the portion of the sheath that has been in contact with the hand of the user from the door handle into a recepticle and moves a portion of the sheath that has not been in contact with the hand of the user over the door handle. In some implementations, the surface sanitizer may be an electrical charge. For example, in some implementations, during a door handle sanitation cycle, door handle sanitizer mechanism 110 may discharge an electrical pulse through the door handle in order to disinfect the door handle. The amount of electrical charge may various, and will depend on the particuluar implementation. In some implementations, the surface sanitizer may be heat. For example, in some implementations, door handle sanitizer mechanism 110 may heat the door handle using any suitable heating mechanism. In some implementations, door handle sanitizer mechanism 110 may heat the door handle using high-temperature air that is heated to at least a predetermined temperature.

Note that the term sanitize may be used in the context of santizing the hand of the user. Also, the terms sanitize and disinfect may be used interchangeably in the context of sanitizing or disinfecting a door handle. In various implementations, sanitation system 100 may sanitize or reduce germs (e.g., harmful bacteria and/or viruses, etc.) on a given surface (e.g., a hand, door handle, surgical tools, as well as other objects) to predetermined levels in order to meet or surpass public health codes and/or regulations. In this sense, in various implementations, the term sanitation may be used in the context of reducing germs whether partially or completely on the hands of a user or on the surface of inanimate objects such as a door handle.

In various implementations, sanitation system 100 may disinfect/decontaminate, destroy and/or inactivate germs (e.g., rendering harmful/pathogenic bacteria and/or viruses inert, etc.) on a given surface (e.g., a door handle, as well as other objects). In this sense, in various implementations, the term disinfect or decontaminate may be used in the context of reducing germs substantially completely (e.g., 99%, 99.9%, 100%, and is not limited to these percentages) on the surface such as a door handle, or other surfaces.

For either sanitaztion or disinfection, the degree or percentage of destroying germs may vary, and will depend on the particular implementation. Also, the amount of time to destroy the germs to a predetermined level may vary, and will depend on the particular implementation.

In various implementations, hand sanitizer mechanism 108 of sanitation system 100 includes a nozzle 112 for applying or dispensing hand sanitizer to the hand of a user, and a fluid tank or fluid reservoir 114 for storing hand sanitizer. Hand sanitizer mechanism 108 also includes a fluid fill port 116 for providing access to fluid reservoir 114 and for adding hand sanitizer to fluid reservoir 114. In various implementations, fluid reservoir 114 may be accessed from the top of the sanitation system unit for refilling.

In some implementations, hand sanitizer mechanism 108 may also include a fluid level indicator for indicating to a user how much hand sanitizer is remaining in fluid reservoir 114. For example, in some implementations, hand sanitizer mechanism 108 may include a fluid level site window (not shown) that enables a user to see the fluid level of fluid reservoir. In some implementations, hand sanitizer mechanism 108 may include fluid level sensor senses when the fluid level drops below a predetermined fluid level. In some implementations, the fluid level drops below a predetermined fluid level may trigger an alert (e.g., an audible sound, a visual indicator, or other indicator).

In various implementations, hand sanitizer mechanism 108 of sanitation system 100 also includes a fluid pump 120 for pumping hand sanitizer from fluid reservoir 114 to nozzle 112. Fluid pump 120 includes a fluid path pump input 122 for receiving hand sanitizer from fluid reservoir 114 and a fluid path pump output 124 for sending hand sanitizer to nozzle 112. In various implementations, fluid pump 120 provides a measured quantity of fluid to the hand by way of a nozzle. Various implementations minimize the quantity of fluid between the nozzle and reservoir in order to efficiently provide hand sanitizer to the hand of the user. Example operations of hand sanitizer mechanism 108 are described in more detail below.

In some implementations, the hand sanitizer may be a gel. In some implementations, the hand sanitizer may be a foam. In some implementations, the hand sanitizer may be a liquid. The particular substance and/or form of the hand sanitizer may vary, and will depend on the particular implementation.

In various implementations, door handle sanitizer mechanism 108 of sanitation system 100 includes a light source 126. As described in more detail herein, light source 126 may be an ultra violet (UV) light source for sanitizing door handle 106. As such, sanitation system 100 is self-cleaning in that it santizes door handle 106. In various implementations, door handle sanitizer mechanism 108 directs energy (e.g., UV light) such that it falls on the entire surface of door handle 106 in a predetermined period of time (e.g., 1 second, 2 seconds, 2.5 seconds, or other time periods).

Various techniques may be used to sanitize or disinfect door handle 106. For example, as shown in FIG. 1, in some implementations, light source 126 may be positioned at a predetermined distance from door handle 106. In various implementations, light source 126 shines UV light against the outside surface of door handle 106 in order to sanitize door handle 106. The distance between light source 126 and door handle 106 may vary, and will depend on the particular implementations. In some implementations, door handle 106 may rotate along its axis in order to expose the entire surface of door handle 106 to light source 126. The degree of rotation may vary, and will depend on the particular implementation. Also, the speed of rotation may vary, and will depend on the particular implementation.

The location and/or position of the light source for sanitizing or disinfecting a door handle may vary, and will depend on the particular implementation. In some implementations, a light source 126 may be positioned inside the door handle. As such, in various implementations, the light source shines UV light against the inside surface of door handle 106. The UV light passes outward through the transparent material of the door handle ultimately making contact the outer surface of the door handle. The UV light making contact with the outer surface disinfects that surface. As such, in addition to sanitation system 100 being self-cleaning, door handle 106 itself may be self-cleaning in that door handle 106 may sanitize itself.

In various implementations, the door handle is translucent in order to enable the UV light to pass through the door handle material in order to sanitize or disinfect the door handle. The material of the door handle may vary, and will depend on the particular implementation. Other example implementations for sanitizing a door handle described in more detail herein.

In various implementations, sanitation system 100 includes a lock mechanism 128 for locking and unlocking door 102. In some implementations, sanitation system 100 may lock door 102 when closed and then unlock door 102 after sanitation system 100 sanitizes the hand of the user (e.g., dispenses hand sanitizer onto the hand of the user).

In various implementations, sanitizer system 100 includes an override button 130, which enables a user to override the normal processes of sanitizer mechanism 100 (e.g., in case of an emergency, or other urgency). Such processes may be overridden in the case of several persons entering a room, through an entry point, at one time, where each person needs sanitizer applied accordingly. Example implementations of override button 130 are described in more detail herein. In various implementations, sanitizer system 100 includes a power supply 132 for providing power to the various components of sanitizer system 100.

In various implementations, sanitizer system 100 includes a controller system 134 for controlling the operations of sanitizer system 100. As described in more detail herein, controller 134 may be implemented by any suitable system such as computing system 1400 described below.

For ease of illustration, FIG. 1, as well other figures herein, show particular components. Some components shown may represent multiple components. Furthermore, in various implementations, figures may not have all of the components shown and/or may have other elements including other types of components instead of, or in addition to, those shown herein.

In various implementations, controller system 134 may also function as sanitation compliance unit or system. As described in more detail herein, the sanitation compliance system monitors usage of sanitizer system 100 and facilitates sanitation compliance. Example implementations of sanitation compliance system are described in more detail herein. In various implementations, controller system 134 includes antennae and a network interface for RFID functionality as well as communication and transmission of compliance information to a central system, or other control system. In various implementations, sanitizer system 100 may transmit sanitation compliance information to a central system using any suitable wireless communication system and/or network (e.g., WIFI, etc.) or wired communication system and/or network.

In some implementations, hand sanitizer mechanism 108 of sanitizer system 100 may provide hand sanitizer to a hand of a user even if the user does not use the door. For example, in some scenarios, a user may approach the sanitizer system 100 in order to apply hand sanitizer, where the user intends to sanitize the users hands and does not intend to use the door.

Figure 2:
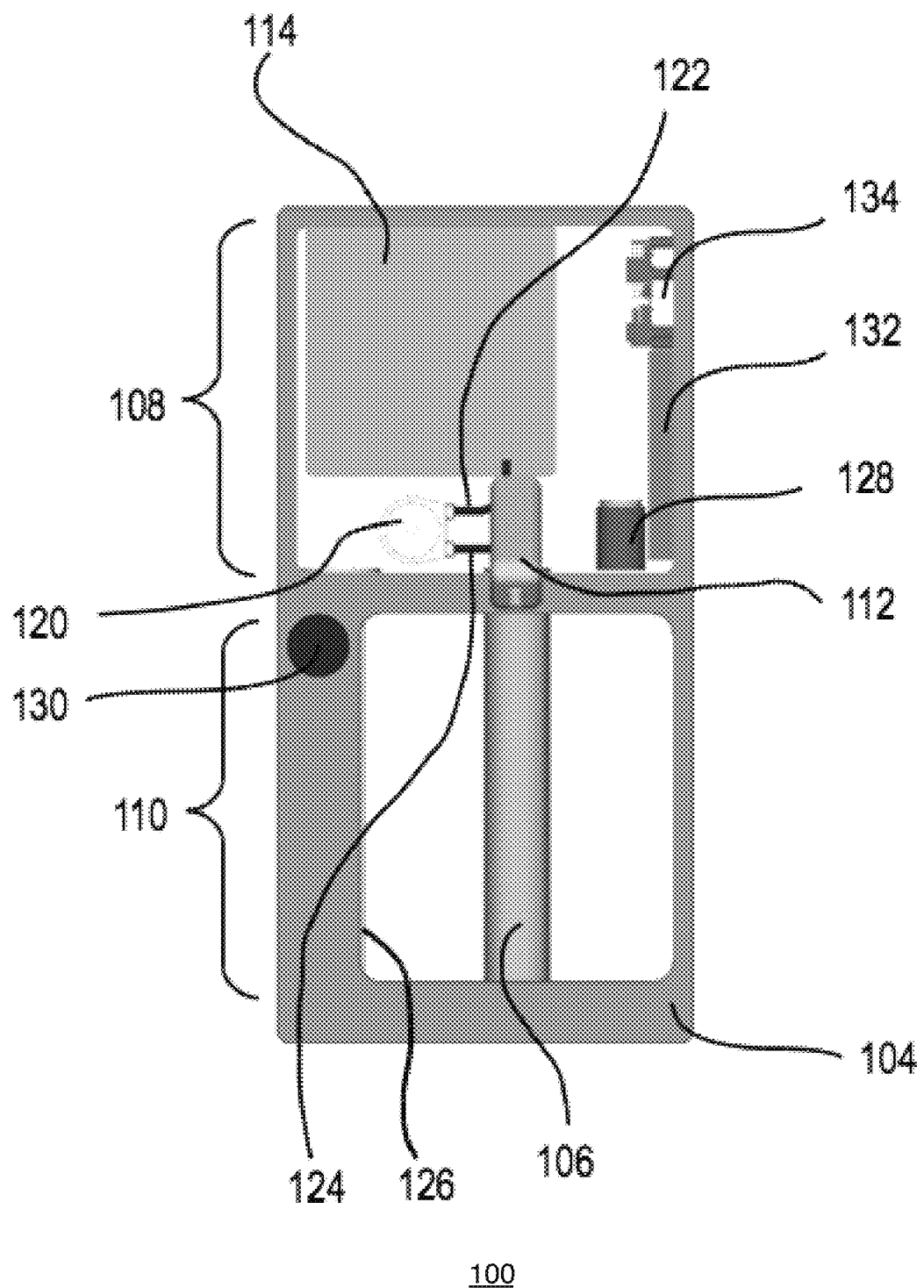
FIG. 2 illustrates a front view of a sanitation system, according to some implementations.

FIG. 2 illustrates a front view of sanitation system 100 of FIG. 1, according to some implementations. Shown in FIG. 2 are base 104, door handle 106, hand sanitizer mechanism 108, door handle sanitizer mechanism 110, nozzle 112, fluid reservoir 114, fluid pump 120, fluid path pump input 122, fluid path pump output 124, light source 126, lock mechanism 128, override button 130, power supply 132, and controller 134.

Figure 3:
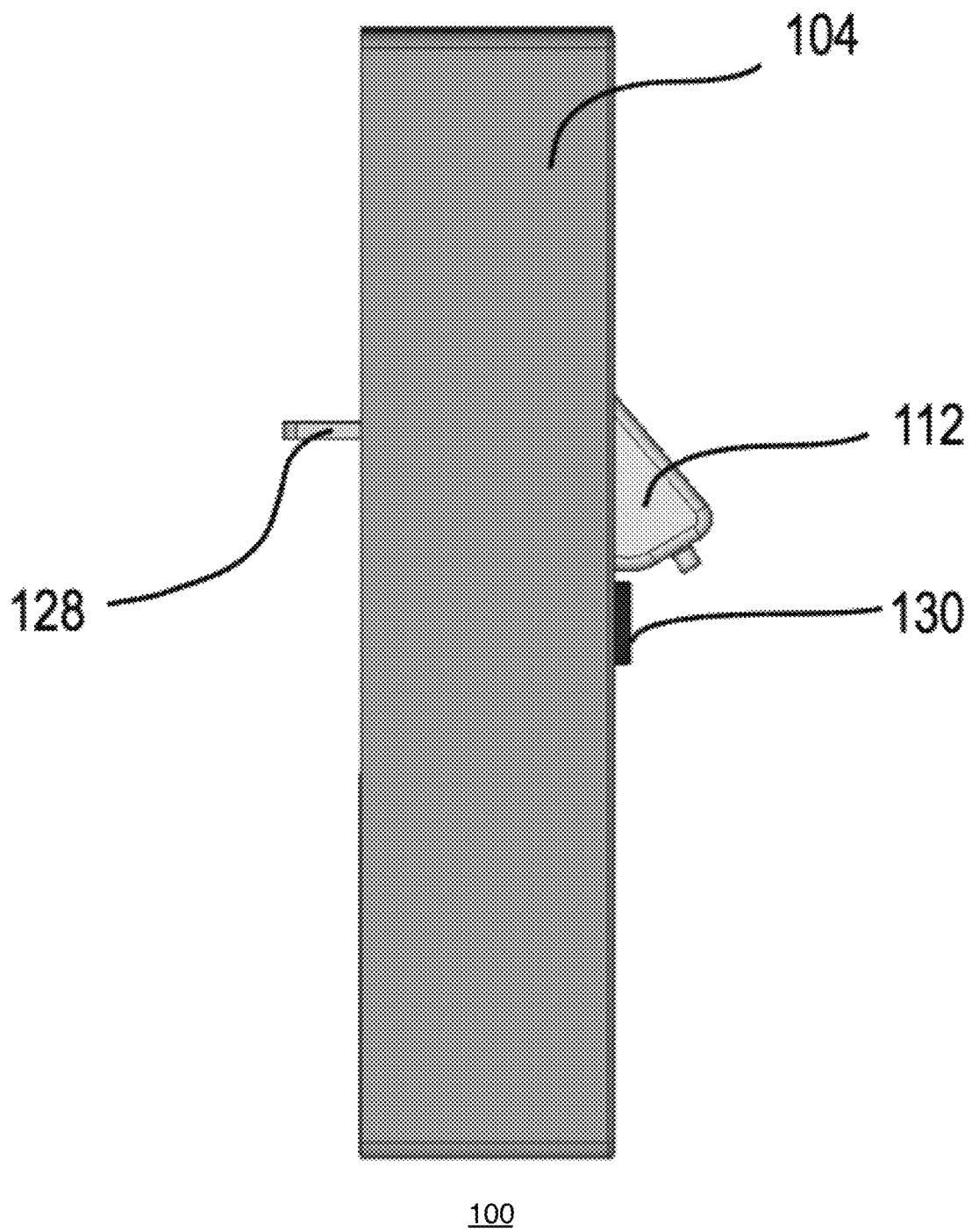
FIG. 3 illustrates a side view of a sanitation system, according to some implementations.

FIG. 3 illustrates a side view of sanitation system 100 of FIG. 1, according to some implementations. Shown in FIG. 3 are base 104, nozzle 112, override button 130, and lock mechanism 128.

Figure 4:
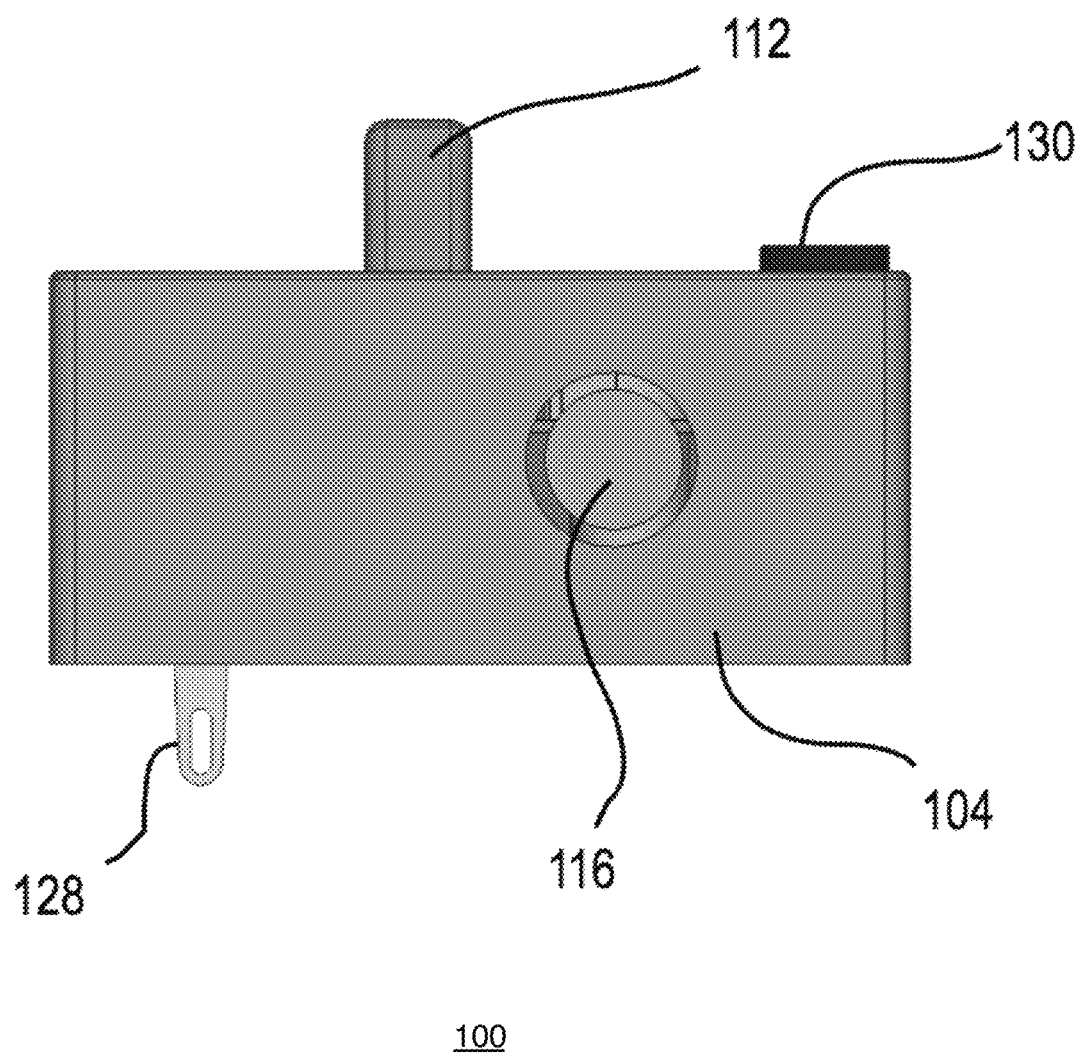
FIG. 4 illustrates a top view of a sanitation system, according to some implementations.

FIG. 4 illustrates a top view of sanitation system 100 of FIG. 1, according to some implementations. Shown in FIG. 4 are base 104, nozzle 112, a fluid fill port 116, override button 130, and lock mechanism 128.

Figure 5:
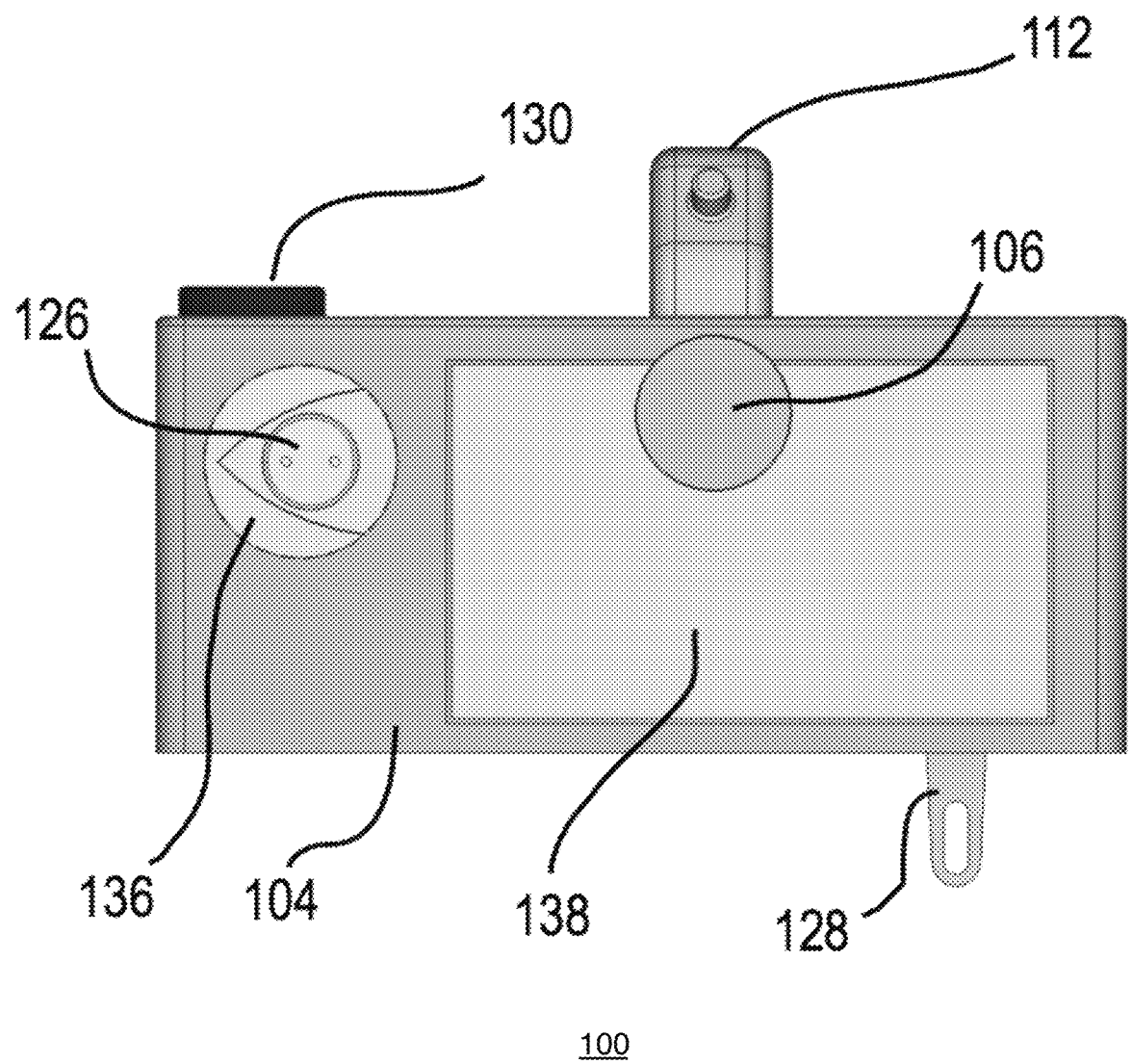
FIG. 5 illustrates a bottom view of a sanitation system, according to some implementations.

FIG. 5 illustrates a bottom view of sanitation system 100 of FIG. 1, according to some implementations. Shown in FIG. 5 are base 104, door handle 106, nozzle 112, override button 130, and lock mechanism 128.

As shown, sanitation system 100 also includes a lamp access port 136 for enabling a user (e.g., a technician, staff member, or other type of user) to replace light source 126, and door handle rotation mechanism 138. As described herein, door handle 106 rotates in order to expose all of its surface to the UV light provided by a light source (e.g., light source 120). In some implementations, door handle rotation mechanism 138 may include a gear (not shown) coupled to door handle 106, where the gear rotates to in turn rotate door handle 106.

In various implementations, sanitation system 100 may be configured as an entry point assembly that is mounted at a door entry point and may be integrated into the door itself. The threshold at which each door is positioned with respect to a given room may be referred to as an entry point. In various implementations, one or more sanitation system units may be implemented at each entry point of rooms in one or more buildings. In various implementations, there may be multiple entry points for a given room, and each entry point may have one or more doors (e.g., single door or double door at each entry point).

In various implementations, the sanitation system unit may be mounted on an internal metal structural bracket meant to attach to the door itself while interfacing with the door mechanism. In various implementations, sanitation system 100 may include a door handle to be used for opening a door, as shown in the example implementation of FIG. 1. As indicated herein, in some implementations, sanitation system 100 may be supplied with electrical power and a network interface for wireless or wired communication to a central system. Various operations of sanitation system 100 are described in more detail herein.

For ease of illustration, various implementations are described herein in the context of sanitation system 100 sanitizing one hand and one door handle. For example, in some implementations, if sanitation system 100 is mounted on a single-door entry point having one door handle, sanitation system 100 may be configured to sanitize the hand that makes contact with the door handle, and to sanitize the door handle. In another example, in some implementations, if sanitation system 100 is mounted on a double-door entry point having two door handles or two door pulls, there may be two sanitation system assemblies, one per door where each sanitation system assembly may be configured to sanitize the hand that makes contact with the respective door handle, and to sanitize the respective door handle. However, these implementations and others may sanitize both hands of a user and/or may sanitize multiple door handles depending on the particular implementation.

In various scenarios, doors in a given building may vary. For example, patient room doors may vary from hospital to hospital and may require a flexible method to interface sanitation system 100. For example, some doors are swinging doors. Some doors are sliding doors. Some doors have a door handle that is a lever, a knob, push bar, pull bar, and is not limited to these types of door handles. Some doors have a mechanical catch. Some doors are self closing.

In some implementations, where an entry point has a slider door, the door handle of sanitation system 100 would experience side forces in use as the user open and closes the door. In some implementations, sanitation system 100 may have an expanded opening to allow for hand articulation. For example, the window or opening in sanitation system 100 may be wider in order to allow the user to grab the door handle at different angles as the door slides open or shut.

In some implementations, where an entry point has no door, sanitation system 100 may be a unit with a hand sanitizer mechanism and a sanitation compliance system, where a handle sanitizer mechanism is not needed. Example implementations of a sanitation compliance system is described in more detail herein. Because there is no door, a door handle sanitizer mechanism would not be needed in this particular implementation. As such, there would be a hand sanitation and sanitation compliance cycle but no door handle sanitation cycle. Such cycles are described in more detail herein. In various implementations, sanitation system 100 may be located in close proximity to the entry point (e.g., on the wall). Instead of detecting when the user grabs a door handle, sanitation system 100 detects when the hand of the user is underneath the nozzle to receive hand sanitizer.

As such, in various implementations, any given unit of sanitation system 100 may include any one or more of hand sanitizer mechanism, door handle sanitizer mechanism, and sanitation compliance system.

In some implementations, sanitation system 100 may be implemented in a highly contagious zone. In some implementations, in a highly contagious zone, sanitation system 100 may sanitize the door handle using a UV light as describe herein. In some implementations, in a highly contagious zone sanitation system 100 may sanitize the door handle using a disinfectant chemical. For example, in various implementations, sanitation system 100 may sanitize the door handle using a chemical (e.g., disinfectant gel, as well as other forms) that exudes chemicals from the handle.

In various implementations, sanitation system 100 and associated techniques and methods may track and confirm compliance with various sanitation procedures and models. Various such implementations are described in more detail below.

Figure 6:
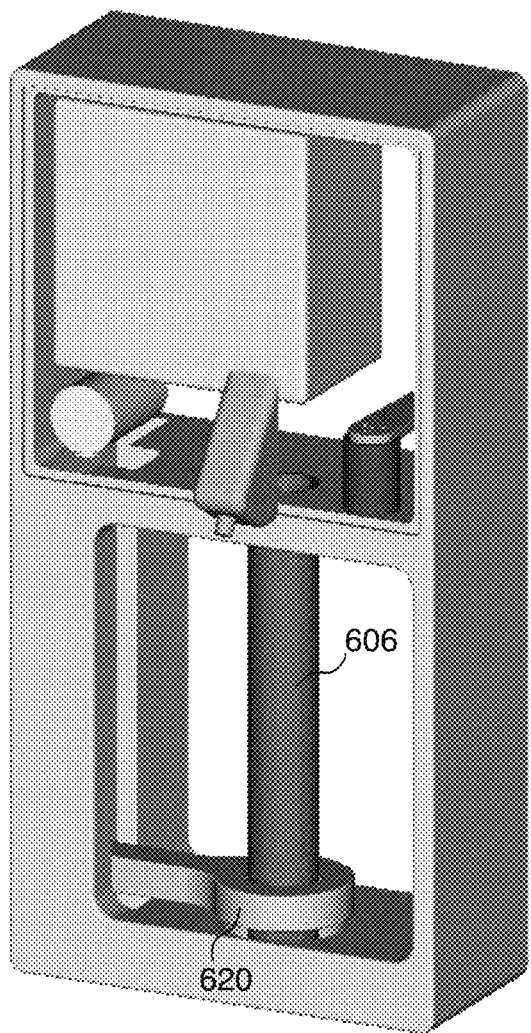
FIG. 6 illustrates a perspective view of a sanitation system, according to some implementations.

FIG. 6 illustrates a perspective view of a sanitation system 600, according to some implementations. Sanitation system 600 may include a hand sanitizer mechanism similar to sanitation system 100 of FIG. 1. As described in more detail herein, in various implementations, the door handle sanitizer mechanism of sanitation system 600 sanitizes the door handle 606 using an annular wand 620.

In some implementations, annular wand 620 surrounds the door handle, where annular wand 620 outputs a UV light toward door handle 606, and where annular wand 620 travels across door handle 606 surface in order to sanitize door handle 606. For example, annular wand 620 may emit a UVC light inwardly toward door handle 606. Because annular wand 620 surrounds door handle 606, the UV light is directed toward door handle 606 from multiple angles (e.g., up to 360 degrees). As annular wand 620 travels along door handle 606, the UV light sanitizes or disinfects different portions of door handle 606 as the UV light makes contact with the outer surface of door handle 606. As indicated herein, the UV light source may be, for example, a UVC LED linear array, UVC fluorescent lamp, as well as other UV light sources. Annular wand 620 may travel vertically (e.g., up and down) in the case of a vertically oriented door handle (e.g., a vertical pull handle) or may travel horizontally (e.g., side to side) in the case of a horizontally oriented door handle (e.g., a horizontal lever handle).

In some implementations, annular wand 620 may output high temperature air that sanitizes door handle 606. In various implementations, sanitation system 600 may include an adjacent heater and fan assembly that provides the high temperature air. As described herein, annular wand 620 may travel across door handle 606 in order to sanitize the entire door handle 606.

In some implementations, annular wand 620 may include a thermal infrared lamp that heats the surface of door handle 606 in order to sanitize door handle 606. As described herein, annular wand 606 may travel across door handle 606 in order to sanitize the entire door handle 606.

Figure 7:
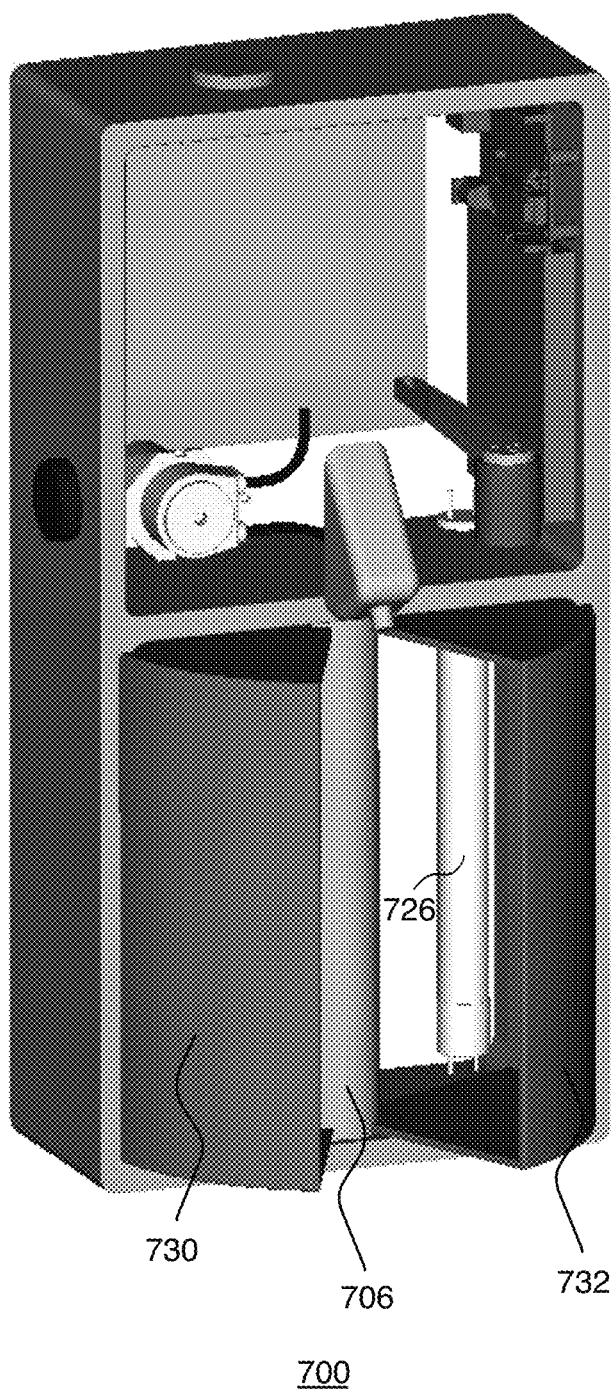
FIG. 7 illustrates a perspective view of a sanitation system, according to some implementations.

FIG. 7 illustrates a perspective view of a sanitation system 700, according to some implementations. Sanitation system 700 may include a hand sanitizer mechanism similar to sanitation system 100 of FIG. 1. As described in more detail herein, in various implementations, the door handle sanitizer mechanism of sanitation system 600 sanitizes the door handle 706 using one or more UV lights. As shown, sanitation system 700 includes a UV light 726 that emits a UVC light toward door handle 706. Sanitation system 700 also includes a second UV light (not shown) that emits a UVC light toward door handle 706. The particular number of UV lights may vary, depending on the particular implementation.

As shown, sanitation system 700 includes two doors 730 and 732 that function to shield UV light from a user while santizing door handle 706. For example, when the user grasps door handle 706, the UV lights are turned off. After the user uses and subsequently releases door handle 706, doors 730 and 732 close.

Figure 8:
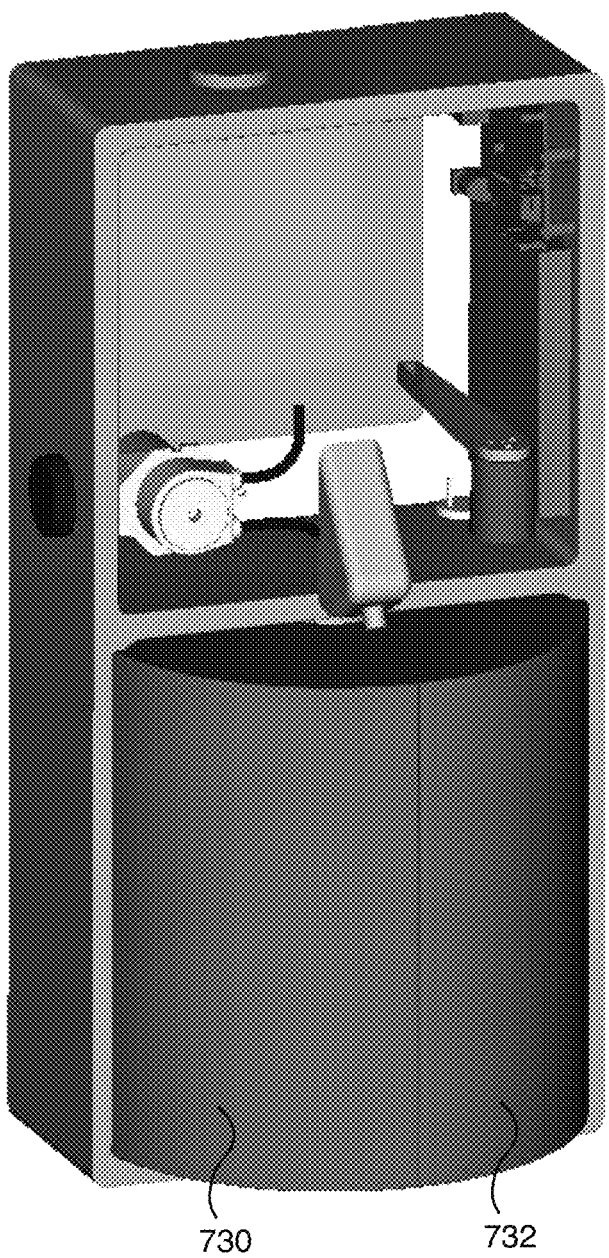
FIG. 8 illustrates a perspective view of the sanitation system of FIG. 7, according to some implementations.

FIG. 8 illustrates a perspective view of sanitation system 700 of FIG. 7, where doors 730 and 732 are closed, according to some implementations. Once doors 730 and 732 close, the UV lights turn on in order to sanitize door handle 706. Because doors 730 and 732 are shut, UV light is unable to escape thereby protecting the eye's of the user. While implementations of sanitation system 700 are described in the context of two doors, these implementations and others may apply to any number of doors such as a single door, where the single door opens and closes in order to shield the UV light. For example, the door may slide open and close or swing open and close. Further the shape or curvature of the door or doors may vary depending on the particular implementation. For example, in some implementations, the door or doors may be curved or flat.

Figure 9:
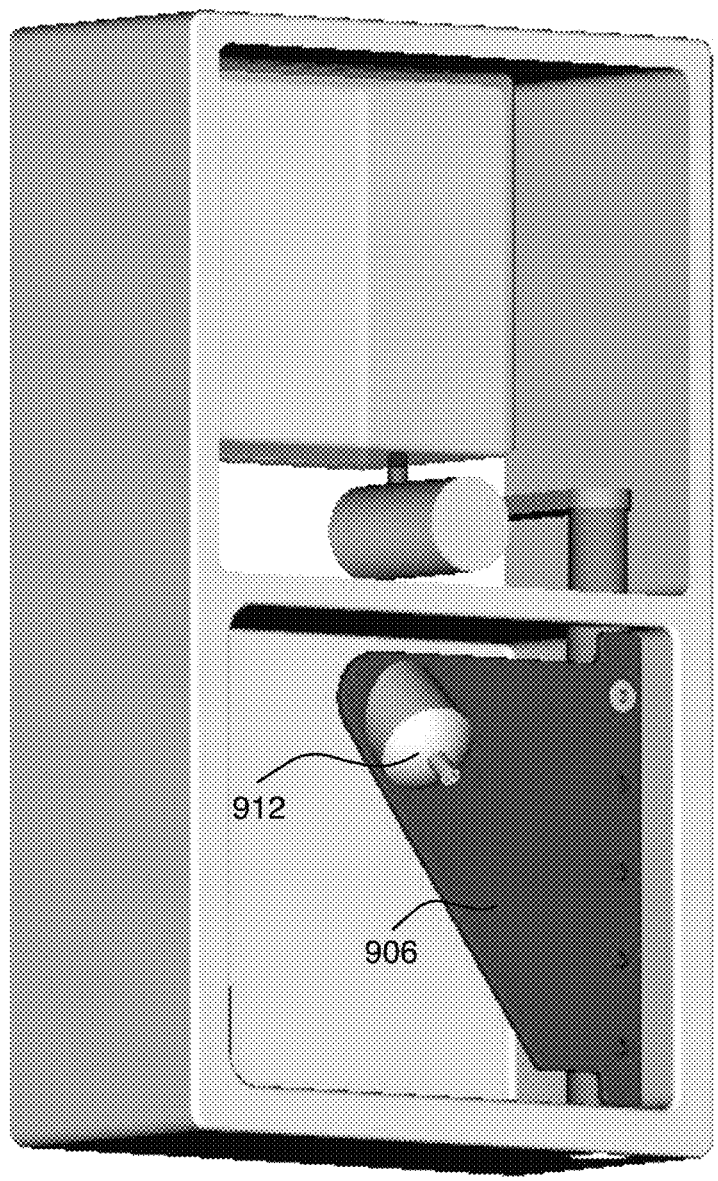
FIG. 9 illustrates a perspective view of a sanitation system, according to some implementations.

FIG. 9 illustrates a perspective view of a sanitation system 900, according to some implementations. Sanitation system 900 includes a hand sanitizer mechanism, where the door handle 906 has a nozzle 912 attached. In some implementations, when the user pulls on door handle 906 with the user's hand in order to operate a door, nozzle 912 applies a hand sanitizer to the user's hand. After the user releases door handle 906, the user can then spread the hand sanitizer over both of the user's hands in order to sanitize the user's hands.

Figure 10:
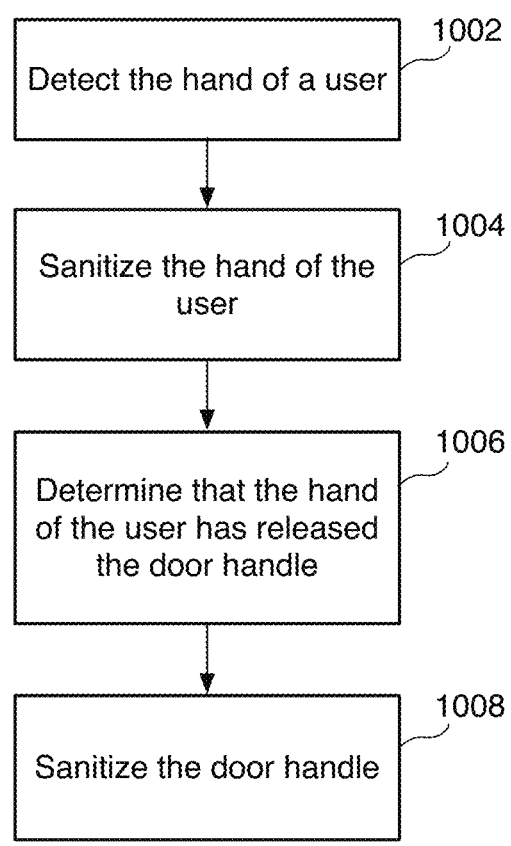
FIG. 10 illustrates a flow diagram for sanitizing at entry points, according to some implementations.

FIG. 10 illustrates a flow diagram for sanitizing at entry points, according to some implementations. Referring to both FIGS. 1 and 10, a method is initiated in block 1002, where sanitation system 100 detects the hand of a user. In some implementations, a detection mechanism detects the hand of the user when the hand is at or within a predetermined distance from door handle 106. Various techniques for detecting the hand may be used, depending on the particular implementation. For example, in some implementations, the detection mechanism of sanitation system 100 may determine that the hand is in a particular location (e.g., at or within a predetermined distance from the door handle), where a sufficiently close distance may be equated with the handle being grasped by the hand. In some implementations, the detection mechanism may detect if the hand is making actual contact with the door handle. Various implementations directed to hand detection are described in more detail herein.

In some implementations, as a user approaches the door, sanitation system 100 may identify the user. Such identification may be used for compliance purposes (e.g., to determine who is complying with sanitation procedures). Such identification may be used for other purposes such as entry permission. The particular uses for identification of the user may vary and will depend on the particular implementation and/or requirements of the facility. Various example implementations directed to identifying a user are described in more detail herein.

In some implementations, sanitation system 100 may provide a status indication, where the status indication indicates if the handle is clean and ready to be touched or grasped. In some implementations, the status indication may be a colored light such a light emitting diode (LED). For example, a green light may indicate "ready" or "clean," and a red light may indicate "not ready" or not yet "clean." Such status information provides immediate feedback to the user on the status of the system. As such, the user may grasp the door handle after ascertaining from the status indication that the door handle is ready for use. Various example implementations directed to status indications are described in more detail herein.

In block 1004, sanitation system 100 sanitizes the hand of the user. As indicated herein, hand sanitizer mechanism 102 of sanitation system 100 is configured to sanitize the hand of the user. In some implementations, when sanitation system 100 detects the hand it applies or ejects hand sanitizer to the user's hand as the hand is grasping door handle 106. As indicated herein, the hand sanitizer may be a gel. In some implementations, the hand sanitizer may be a foam. The user may then spread the hand sanitizer to the user's other hand, spreading the hand sanitizer over the entire surface of both hands. As a result, sanitation system 100 facilitates sanitization of both hands of the user. Various example implementations directed to hand sanitation are described in more detail herein.

In some implementations, sanitation system 100 enables the user to open the door. In various implementations, sanitation system 100 enables the user to open the door by unlocking a door lock mechanism associated with the door. As such, the user may then open the door using the door handle. In some implementations where sanitation system 100 includes an integral lock system, sanitation system 100 unlocks the door to enable the user to open the door. The user may then actuate the door handle and pull or push the door open to enter. After releasing the door handle, the user may then wipe their hands together as with normal sanitizer use.

As described in more detail below, the user may actuate the door handle in a variety of ways in order to open the door, depending on the door handle. For example, actuation may involve the hand of the user turning a lever of a lever type door handle. In another example, actuation may involved the hand of the user pushing or pulling a pull type door handle. Various implementations direct to door handles are described in more detail herein.

In block 1006, sanitation system 100 determines that the hand of the user has released door handle 106. In some implementations, sanitation system 100 may determine that the hand of the user has released the door handle by sanitation system 100 no longer detecting the hand of the user. In an example scenario, at a first or initial moment in time (e.g., T=0), sanitation system 100 does not detect a hand. Then, at a second or subsequent moment in time (e.g., T=1), sanitation system 100 detects a hand (e.g., as in block 1002). Then, in a third or subsequent moment in time (e.g., T=2), sanitation system 100 no longer detects the the hand. In other words, there is a moment of non-detection, followed by a moment of detection, followed by a moment of non-detection. The second instance of non-detection may be considered no longer detecting the hand.

In another example scenario, in some implementations, when sanitation system 100 initially detects the hand of the user in block 1002, sanitation system 100 may generate a signal (e.g., a binary "1") indicating that the hand of the user has been detected. When the hand of the user is no longer detectable, sanitation system 100 may generate a signal (e.g., a binary "0") indicating that the hand of the user is no longer detected. If the hand of the user being no longer detected, sanitation system 100 determines the absence of the hand of a user. In such a scenario, a binary pattern of "01" may be considered a state of no longer detecting the hand. As such, sanitation system 100 may render the door handle to have been released by the hand of the user.

In block 1008, sanitation system 100 sanitizes door handle 106. As indicated herein, door handle sanitizer mechanism 110 of sanitation system 100 is configured to sanitize the door handle.

In some implementations, after sanitation system 100 performs this self clean process (e.g., sanitizing the door handle), sanitation system 100 may display a status indication (e.g., green light) indicating that the door (e.g., door handle) is ready for use. Various implementations directed to sanitizing door handles are described in more detail herein.

In various implementations, sanitation system 100 logs the sanitation cycle. In various implementations, the sanitation cycle may include the instance of the hand sanitation of a particular hand and the instance of the door handle sanitation following the hand sanitation.

In various implementations, sanitation system 100 logs compliance information associated with the sanitation cycle. For example, sanitation system 100 may determine and log one or more of a tuple of compliance information such as time, location, identification (ID) of the sanitation system 100 unit or any ID associated with the entry point, status and/or completion of a sanitation cycle, ID of the user, such as a physician, nurse, administrator, as well as other types of users. In some implementations, sanitation system 100 may send or relay the compliance information to a central system or network computer for monitoring. Various example implementations directed to compliance are described in more detail herein.

Although the steps, operations, or computations may be presented in a specific order, the order may be changed in particular implementations. Other orderings of the steps are possible, depending on the particular implementation. For example, in some implementations, sanitation system 100 may enable the user to open the door before sanitizing the hand, where sanitation system 100 sanitizes the hand as the user opens the door. In some particular implementations, multiple steps shown as sequential in this specification may be performed at the same time. For example, sanitation system 100 may log the sanitation cycle as sanitation system 100 sanitizes the door handle. Also, some implementations may not have all of the steps shown and/or may have other steps instead of, or in addition to, those shown herein. For example, in some implementations, sanitation system 100 may sanitize the door handle and not sanitizes the hands, and vice versa. In some implementations, sanitation system 100 may sanitize the hands and the door handle and not log the sanitation cycle. Other combinations and variations are possible, depending on the particular implementation.

Note that in various implementations described herein, when sanitation system 100 sanitizes the hand, sanitation system 100 applies hand sanitizer to at least one hand of the user. The user may then rub both hands together in order to spread the hand sanitizer to both hands, thereby sanitizing both hands.

Implementations described herein enable personnel (e.g., the user) to approach a room (e.g., a patient room) knowing that, "I can open this door with this unit," "I can sterilize my hands with this unit," "I can touch a clean handle with this unit," etc.

In various implementations, sanitation system 100 may sanitize a hand by applying sanitizer to a predetermined portion of the hand. For example, in some implementations, sanitation system 100 may apply a sanitizer to the side of the hand. More specifically, sanitation system 100 may apply a sanitizer between the thumb and forefinger behind the knuckles of the hand while the door handle is being grasped. The user will clearly see its location and know that it will not spill off with their hand oriented as when un-grasping the handle. After entering the room, the user may bring both hands together to spread the sanitizer over both hands.

In some implementations, the particular type of hand sanitizer may vary and will depend on the particular implementation. For example, in some implementations, the hand sanitizer may be a topical solution.

In various implementations, sanitation system 100 may sanitize a door handle in a variety of ways. Implementations provide a point of entry hand cleaning station that interacts with the user entering the room. As indicated herein, in some implementations, sanitation system 100 may identify the user, may notify one or more users of the system status, as well as take other actions with regard to one or more users.

In some implementations, after the door handle is used to enter the room, a wait time begins while the handle is being decontaminated. Regardless of personnel hand cleaning practice, the door handle will not pass contamination from one person to another due to the door handle being decontaminated. Once the door handle is sanitized/decontaminated/disinfected, the door may be re-accessed by the next user who will clearly see it is in a ready state (e.g., green light indicator). In various implementations, the "wait time" consists of a rapid decontamination of the handle. This specific process step may be performed by any of several methods described herein.

In some implementations, sanitation system 100 may include a door handle that is configured to output a sanitizer when grasped. In some implementations, the door handle may exude a sanitizer when the hand of the user applies pressure to the door handle (e.g., squeezes the door handle). After the user opens the door (e.g., pulling or pushing the door handle, as well as other motions), the user may subsequently release the hand from the door handle and then wipe both hands together to sanitize both hands.

In various implementations, sanitation system 100 may include a transparent door handle, where sanitation system 100 causes an ultraviolet (UV) light to pass through the door handle, where the UV light sanitizes the door handle.

In various implementations, the UV light falls within a predetermined wavelength range. For example, in some implementations, the UV light may be a UVC light (e.g., 280 nanometers (nm)-100 nm). The particular type of UV light may vary, depending on the particular implementation. For example, the UV light may be a UVA light (e.g., 400 nm-320 nm) or UVB light (e.g., 320 nm-280 nm).

In various implementations, the door handle may include an LED array that outputs a UV light that sanitizes the door handle. For example, in some implementations, the door handle may be a hollow UV transparent thick walled tube with an internal UVC LED linear array inside. As such, the UVC passes through the tube in order to sanitize the outer surface of the tube/door handle. In various implementations, sanitation system 100 may cause the door handle to rotate at least one revolution in order to sanitize the entire door handle.

In some implementations, the door handle may rotate, where rotation of the door handle enables the UVC light to make contact and sanitize the entire outer surface of the door handle. In various implementations, sanitation system 100 may cause the door handle to rotate at least one revolution in order to sanitize the entire door handle. The degree of rotation may vary, and will depend on the particular implementation. For example, in some implementations, the degree of rotation may be a full rotation (e.g., 360 degrees) minus the degree of coverage (e.g., 45 degrees, and other degree values) of the light source. Rotation of the door handle may also apply to other door handle implementations described herein.

In some implementations, the door handle may include fluorescent lamp that outputs a UV light that sanitizes the door handle. For example, in some implementations, the handle may be a hollow UV transparent thick walled tube with an internal UVC baffled fluorescent lamp inside. In various implementations, sanitation system 100 may cause the door handle to rotate at least one revolution in order to sanitize the entire door handle.

In some implementations, the door handle may be coated with a material having sanitation properties. For example, in some implementations, the door handle may be a solid tube with a zinc oxide coating material. In some implementations, the UV light source may be positioned at a predetermined distance from the door handle. As indicated herein, the UV light source may be, for example, a UVC LED linear array, UVC fluorescent lamp, as well as other types of UV light sources. For example, in some implementations, a UV light source may be positioned adjacent to the door handle approximately 75 millimeters (mm), where the UVC light contacts the outer surface of the door handle in order to sanitize the door handle. In various implementations, sanitation system 100 may cause the door handle to rotate at least one revolution in order to sanitize the entire door handle.

In some implementations, sanitation system 100 may include a concentric outer tube, where the concentric outer tube travels across the door handle and wipes the handle with a sanitizer (e.g., germicidal alcohol, etc.), which sanitizes the door handle.

In some implementations, sanitation system 100 may include an adjacent wiper blade that presses against the handle surface as the door handle rotates. The wiper blade may apply a sanitizer (e.g., germicidal alcohol, etc.) to the door handle as the door handle rotates, which sanitizes the door handle.

Figure 11:
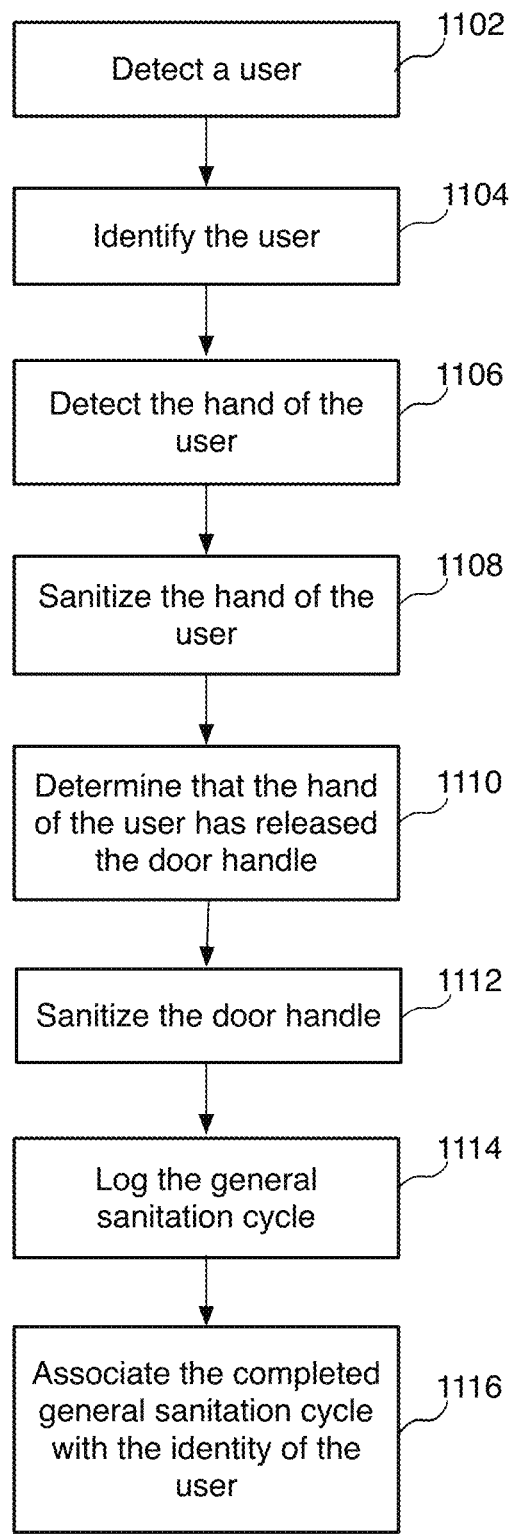
FIG. 11 illustrates a flow diagram for facilitating sanitation compliance at entry points, according to some implementations.

FIG. 11 illustrates a flow diagram for facilitating sanitation compliance at entry points, according to some implementations. Referring to both FIGS. 1 and 11, a method is initiated in block 1102, where sanitation system 100 detects a user. For example, as a user (e.g., hospital personnel, etc.) approaches sanitation system 100, which is attached to a door at an entry point (e.g., door of a hospital patient room, or any other type of room or space), detection system of sanitation system 100 detects the user. Various types of detection system may be implemented at each sanitation system 100 to detect users, depending on the particular implementation. For example, in some implementations, a detection system may be a radio frequency identification (RFID) system.

In various implementations, a sensor of the detection system of sanitation system 100 may detect the RFID tag as the user approaches sanitation system 100. The detection range may vary and will depend on the particular implementation. In various implementations, an RFID reader of the detection system of sanitation system 100 may record the information of the RFID tag for further processing.

In some implementations, sanitation system 100 may perform an RFID loop, where sanitation system 100 broadcasts an RFID signal and receives a response from one or more RFID tags. In some scenarios, if sanitation system 100 receives responses from a given RFID tag for longer than a predetermined time period (e.g., 1 second, 2 seconds, 3 seconds, or other time period), the user associated with that RFID tag is probably at the entry point. It can be assumed that the user intends to pass through the entry point. In some scenarios, if sanitation system 100 receives responses from a given RFID tag for shorter than a predetermined time period (e.g., 0.25 seconds, 0.50 seconds, or other time period), the user associated with that RFID tag was probably walking by or had changed his or her mind about passing through the entry point.

In some implementations, the detection of a user (or RFID loop) may be triggered by a predetermined event. For example, the predetermined event may be the user grasping the door handle, or the hand of a user being detected within a predetermined distance from the door handle.

In block 1104, sanitation system 100 identifies the user. For example, in some implementations, where a detection system is an RFID system, each user may wear an RFID tag (e.g., on an employee badge, or other object that a user may carry or wear), which includes an RFID tag chip that stores identifying information associated with the user. For example, in some implementations, the RFID tag may store identification information (e.g., the users name, employee number, as well as other ID information). In some implementations, the RFID tag may store categorical information such as the users title (e.g., physician, nurse, administrator, or other titles).

The particular types of identification techniques may vary, and will depend on the particular implementation, such as those described herein. In example, in addition to or in lieu of an RFID system, other systems such as biometric and/or facial recognition systems may also be used to identify the user.

In block 1106, sanitation system 100 detects the hand of the user. The particular hand detection techniques may vary, and will depend on the particular implementation, such as those described herein. In some implementations, if the sanitation system 100 does not detect the hand of the user, sanitation system 100 within a predetermined time period (e.g., 1 second, 2 seconds, 3 seconds, or other time period), sanitation system 100 determines if the user is still detected to be in close proximity. If the user is still detected, sanitation system 100 may continue to wait and periodically determine if the user is still detected. If sanitation system 100 then detects the hand of the user, and the user has been continually detected, the process continues. For example, the user may be in close proximity but might not enter immediately, perhaps due to a brief conversation with another person just before the user actually grabs the door handle.

If the user is no longer detected, sanitation system 100 waits for detection of a subsequent user. For example, there may be scenarios where a user is detected but the user is simply walking by the sanitation system unit and has no intention of entering, or the user changes his or her mind about entering.

In block 1108, sanitation system 100 sanitizes the hand of the user. The particular hand sanitation techniques may vary, and will depend on the particular implementation, such as those described herein.

In block 1110, sanitation system 100 determines that the hand of the user has released the door handle. The particular techniques for determining that the hand of the user has release the door handle may vary, and will depend on the particular implementation, such as those described herein.

In block 1112, sanitation system 100 sanitizes the door handle. The particular door handle sanitation techniques may vary, and will depend on the particular implementation, such as those described herein.

In block 1114, sanitation system 100 logs the general sanitation cycle. For example, in various implementations, sanitation system 100 logs that the general sanitation cycle has been completed. In some implementations, if the general sanitation cycle was not completed for some reason (e.g., an override process was activated, or other event occurred), sanitation system 100 may log that the general sanitation cycle started but was not completed.

In block 1116, sanitation system 100 associates the completed general sanitation cycle with the identity of the user. For example, in various implementations, sanitation system 100 logs that the general sanitation cycle has been completed and also logs the name of the user. In some implementations, sanitation system 100 may log that the general sanitation cycle has been completed. Such information may be referred to as usage information. In various implementations, sanitation system 100 at each entry point may log various types of usage information. For example, usage information may include the type of user who interacted with the sanitation system 100 (e.g., physician, nurse, administrator, etc.) during the general sanitation cycle. In some implementations, the usage information may include one or more times associated with the general sanitation cycle. For example, such times may include the duration of a general sanitation cycle, and/or the duration of a hand sanitation cycle and/or a door handle sanitation cycle. Such time may include date stamps and time stamps of the cycles. A hand sanitation cycle and a subsequent door handle sanitation cycle may be considered subcycles of a general sanitation cycle. Example implementations, of hand sanitation cycles and door handle sanitation cycles are described in more detail herein.

In various implementations, system usage information may also include various compliance information such as instances of general sanitation cycles and associations between such instances and users (e.g., hospital personal, etc.). The types of usage information that is also categorized as compliance information may vary, and will depend on the particular implementation. In various implementations, such usage information, including any compliance information, may be stored to a data file for further processing. As such, sanitation system 100 may integrate sanitation and tracking at a specific location (e.g., entry point to a particular room or area).

In various implementations, sanitation compliance is monitored at each entry point (e.g., at each door installation). In some implementations, sanitation compliance is also monitored at a central system. For example, the sanitation system units in a given building may send system usage information, including compliance information, to the central system for central monitoring and further processing. As such, sanitation system 100 may integrate sanitation and tracking at multiple locations (e.g., entry points of multiples rooms of one or more floors of one or more buildings).

In various implementations, sanitation system 100 may include the use of indicators for the user. For example, in some implementations, sanitation system 100 may have a green light that indicates that sanitation system 100 is not currently performing a door handle sanitation cycle. The green light may indicated to the user that the user can operate (e.g., grasp) the door handle.

In some implementations, sanitation system 100 may have a red light that indicates that sanitation system 100 is currently performing a door handle sanitation cycle. The red light may indicated to the user that the user wait until the red light turns off before operating (e.g., grasping) the door handle. In some implementations, lights with labels (e.g., "Okay to use," "Wait," etc.) may be used in lieu of green and red lights.

In some implementations, if sanitation system 100 is currently performing a door handle sanitation cycle, and sanitation system 100 detects the hand of the user at the door handle, sanitation system 100 may automatically stop performing the door handle sanitation cycle.

Although the steps, operations, or computations may be presented in a specific order, the order may be changed in particular implementations. Other orderings of the steps are possible, depending on the particular implementation.

As indicated above, various example implementations facilitate in helping personnel in complying to various sanitation procedures and requirements. In some implementations, while personnel are at a given entry point location (e.g., in proximity to a given sanitation system 100 unit), sanitation system 100 may employ a tracking system that monitor sanitation compliance information, which may include one or more sanitation-associated parameters for compliance. For example, such parameter may include the use of a hand sanitizer, contact with a door handle, a door handle operation sequence, door access, fluid use count, a sanitation system unit ID, the date and time at which a door handle is actuated, over ride conditions, ready/not ready status, detection of a user ID. In various implementations, a central system may collect/receive compliance information from one or more sanitation system units. The central system may store all relevant compliance information for ready interrogation to assist monitoring, training, issues, maintenance, compliance to protocol, acceptance, etc.

Figure 12:
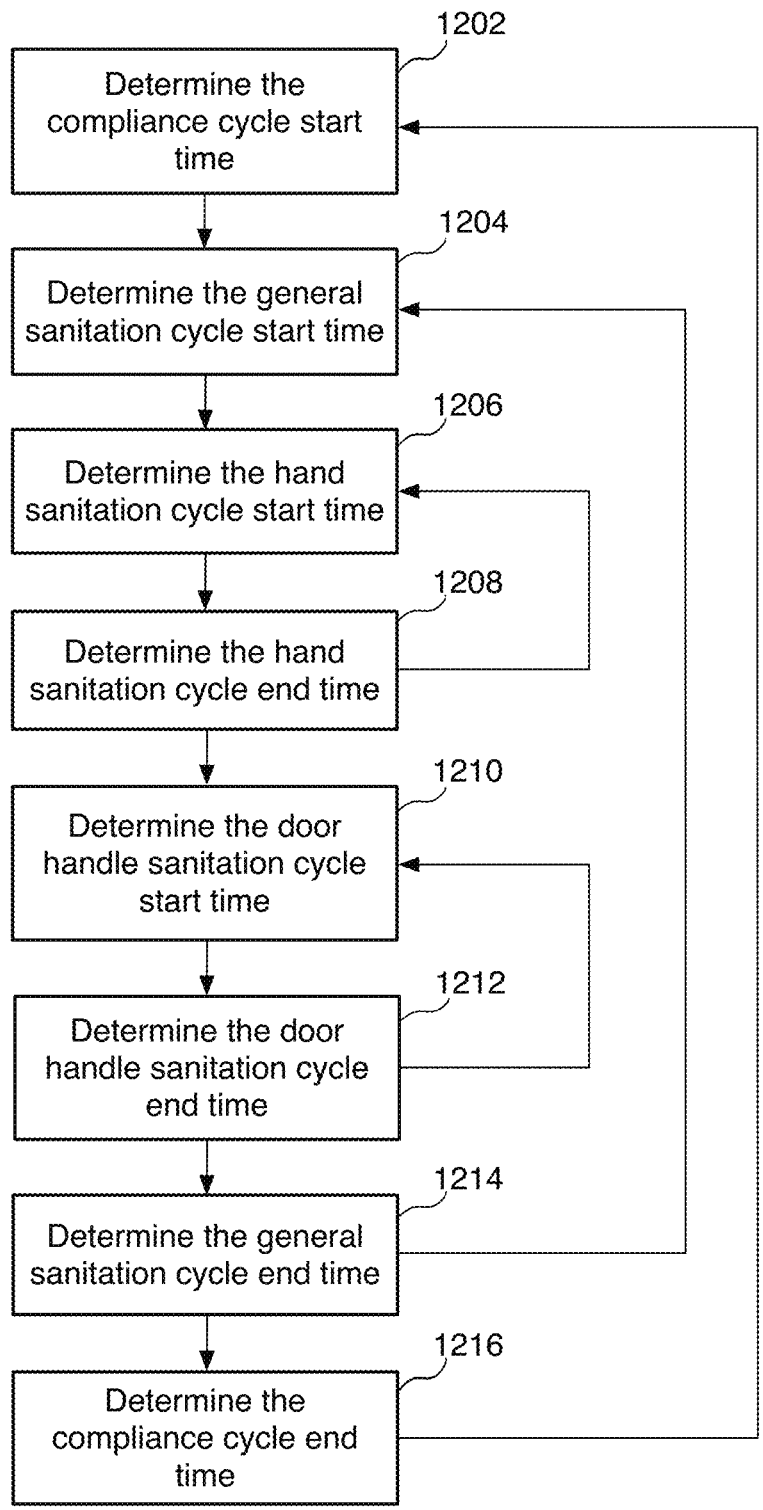
FIG. 12 illustrates a flow diagram for tracking sanitation metrics at entry points, according to some implementations.

FIG. 12 illustrates a flow diagram for tracking sanitation metrics at entry points, according to some implementations. Referring to both FIGS. 1 and 12, a method is initiated in block 1202, where sanitation system 100 determines the compliance cycle start time. In various implementations, the compliance cycle includes the time during which the general sanitation cycle occurs. The general sanitation cycle is described in more detail herein.

In some implementations, the compliance cycle start time may be the time when the user is detected. In some implementations, the compliance cycle start time may be the time when the user is identified. In some implementations, the compliance cycle start time may be the same as the general sanitation cycle start time. In some implementations, the compliance cycle start time may be the time when the hand of the user is detected. The particular compliance cycle start time may vary, and will depend on the particular implementation.

In block 1204, sanitation system 100 determines the general sanitation cycle start time. In various implementations, the general sanitation cycle is the time during which hand sanitation cycle and subsequent door handle sanitation cycle occur. The hand sanitation cycle and door handle sanitation cycle are described in more detail herein.

In some implementations, the general sanitation cycle start time may be the time when the user is detected. In some implementations, the general sanitation cycle start time may be the same as the hand sanitation cycle start time. The particular general sanitation cycle start time may vary, and will depend on the particular implementation.

In block 1206, sanitation system 100 determines the hand sanitation cycle start time. In various implementations, the hand sanitation cycle is the time during which sanitation system 100 sanitizes the hand of the user. As such, in various implementations, the hand sanitation cycle start time is the time that the hand sanitation mechanism of sanitation system 100 begins sanitizing the hand of the user. In some implementations, the hand sanitation cycle start time may be the time when the hand of the user is detected. The particular hand sanitation cycle start time may vary, and will depend on the particular implementation.

In some implementations, sanitation system 100 may also determine door cycles. For example, sanitation system 100 may determine when the door starts to open (e.g., a door open start time or door closed end time), starts to close (e.g., a door closing start time), and when the door is closed (e.g., a door closed start time). Such times may be useful for calibration of devices used during the hand sanitation cycle and during door handle sanitation cycle.

In block 1208, sanitation system 100 determines the hand sanitation cycle end time. In some implementations, the hand sanitation cycle end time may be the time when the hand sanitation mechanism of sanitation system 100 has applied a hand sanitizer to the user. In some implementations, the hand sanitation cycle end time may be the time when sanitation system 100 determines that the hand of the user has released the door handle. The particular hand sanitation cycle end time may vary, and will depend on the particular implementation.

In various implementations, after sanitation system 100 completes the hand sanitation cycle end time, hand sanitation mechanism of sanitation system 100 may go into at least a partial standby state awaiting the next hand sanitation cycle start time.

In block 1210, sanitation system 100 determines the door handle sanitation cycle start time. In various implementations, the door handle sanitation cycle is the time during which sanitation system 100 sanitizes the door handle. As such, in various implementations, the door handle sanitation cycle start time is the time that the door handle sanitation mechanism of sanitation system 100 begins sanitizing the door handle. This may be, for example, when the door handle sanitation mechanism begins to apply a UV light to the door handle.

In some implementations, the door handle sanitation cycle start time may be the time when sanitation system 100 determines that the hand of the user has released the door handle. In some implementations, the door handle sanitation cycle start time may be the same as the hand sanitation cycle end time if sanitation system 100 has determined that the hand of the user has released the door handle. The particular door handle sanitation cycle start time may vary, and will depend on the particular implementation.

Once sanitation system 100 determines the absence of the hand of a user, the door handle is exposed and no longer receiving potential bacteria and/or viruses from the user. As such, door handle sanitation mechanism of sanitation system 100 may begin sanitizing the door handle. Furthermore, sanitation system 100 begins sanitizing the door handle after the hand of the user has released the door handle so as to avoid the door handle sanitation mechanism from sanitizing the hand.

In some scenarios, the hand of the user may release the door handle before the door begins to close. This may be the case, for example, when the door automatically closes. This may be the case in most instances. In some scenarios, the hand of the user may released the door handle after closing the door. This may be the case, for example, when the door does not automatically close, and the user needs to close the door. As such, in various implementations, sanitation system 100 determines the door closing start time and determines the door closed end time. As indicated herein, such times may be useful for calibration of devices used during the hand sanitation cycle and during door handle sanitation cycle.

In block 1212, sanitation system 100 determine the door handle sanitation cycle end time. In some implementations, the door handle sanitation cycle end time may be the time when the door handle sanitation mechanism of sanitation system 100 has sanitized/disinfected the door handle. In some implementations, the door handle sanitation cycle end time may be the time at the end of a predetermined time period after the door handle sanitation cycle start time. This may be, for example, the time at the end of a predetermined time period after the door handle sanitation mechanism begins to apply a UV light to the door handle. The particular door handle sanitation cycle end time may vary, and will depend on the particular implementation.

In various implementations, after sanitation system 100 completes the door handle sanitation cycle end time, the door handle sanitation mechanism of sanitation system 100 may go into at least a partial standby state awaiting the next door handle sanitation cycle start time.

In block 1214, sanitation system 100 determines the general sanitation cycle end time. In some implementations, the general sanitation cycle end time may be the same time as the door handle sanitation cycle end time. The particular general sanitation cycle end time may vary, and will depend on the particular implementation.

In various implementations, after sanitation system 100 completes the door handle sanitation cycle end time, sanitation system 100 may go into at least a partial standby state awaiting the next general sanitation cycle start time.

As indicated herein, after completion of the general sanitation cycle, sanitation system 100 logs or records that the general sanitation cycle has been completed and also logs the name of the user. This process may be part of the compliance cycle. Such compliance information may be stored to a data file for further processing (e.g., sent to a central server for processing, etc.).

In block 1216, sanitation system 100 determines the compliance cycle end time. In some implementations, the compliance cycle end time may be the same time as the general sanitation cycle end time. The particular compliance cycle end time may vary, and will depend on the particular implementation. In some scenarios, at the time of the compliance cycle end time, sanitation system 100 might no longer detect the presence of user. In some implementations, sanitation system 100 may determine that time in which sanitation system 100 no longer detects the presence of user. From this determination, sanitation system 100 may further determine that the user has already passed through the entry point, and complied with sanitation procedures.

In various implementations, after sanitation system 100 completes the compliance cycle end time, sanitation system 100 may go into at least a partial standby state awaiting the next compliance cycle start time.

Although the steps, operations, or computations may be presented in a specific order, the order may be changed in particular implementations. Other orderings of the steps are possible, depending on the particular implementation.

As indicated herein, sanitation system 100 may store system usage information, including compliance information, in a data file for further processing. In various implementations, a data file may include a sanitation system unit number, a location (e.g., floor number, section number, room number, door number), a user ID, a user name, a date stamp, a time stamp, a completion indication, any times associated with a hand sanitation cycle, any times associated with a door handle sanitation cycle, any times associated with a sanitation compliance cycle. Any combination of any one or more of these types of information may be included in a data file. The particular types of information included in a data file may vary, and will depend on the particular implementation.

Other types of information are possible. For example, the data may include a fluid level indication to indicate if more sanitizer needs to be added to the sanitation system.

While sanitation system 100 is described as performing the steps as described in the embodiments herein, any suitable component or combination of components of sanitation system 100 or any suitable processor or processors associated with sanitation system 100 may facilitate in performing at least some of the steps described. Various other modes of operation may be implemented such as periodic maintenance, handle wipe down, germicidal replenishment, emergency override, as well as other modes of operation.

Implementations described herein provide various benefits. For example, implementations described herein enable and facilitate hand cleaning compliance and actively suppress transmission of pathogens. Implementations enable tracking of personnel compliance with regard to sanitation compliance procedures and requirements, overriding door lock mechanisms for emergencies and special circumstances. Implementations provide integrated standalone units that can be networked.

Figure 13:
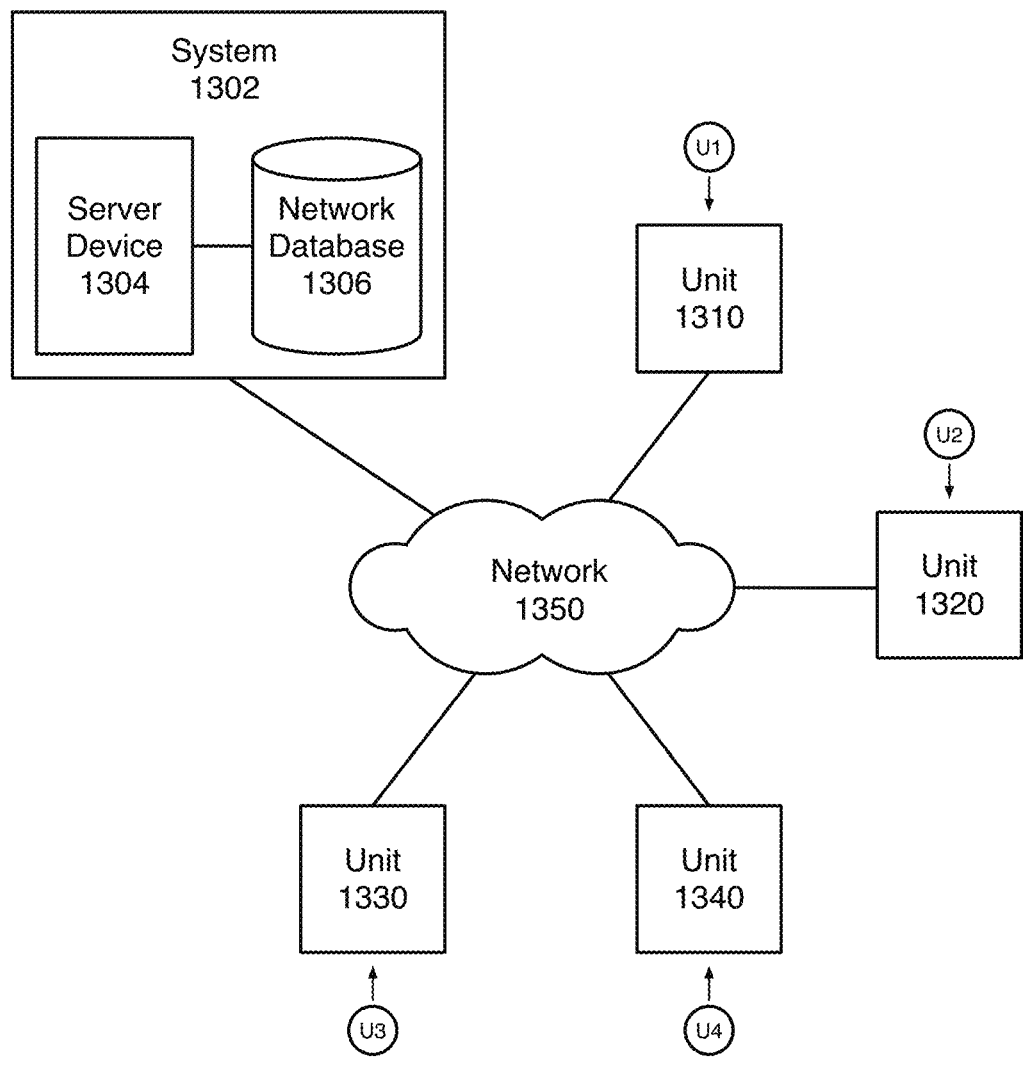
FIG. 13 illustrates a block diagram of an example network environment, which may be used for some implementations described herein.

FIG. 13 illustrates a block diagram of an example network environment 1300, which may be used for some implementations described herein. In some implementations, network environment 1300 includes a system 1302, which includes a server device 1304 and a network database 1306. Network environment 1300 also includes units 1310, 1320, 1330, and 1340, which communicate with system 1302. Network environment 1300 also includes a network 1350. In various implementations, units 1310, 1320, 1330, and 1340 may function as nodes or client devices and communicate with server device 1304 of system 1302 via network 1350. For example, units 1310, 1320, 1330, and 1340 may collect, store, and then send compliance information to system 1302.

For ease of illustration, FIG. 13 shows one block for each of system 1302, server device 1304, and network database 1306, and shows four blocks for units 1310, 1320, 1330, and 1340. Blocks 1302, 1304, and 1306 may represent multiple systems, server devices, and network databases. Also, there may be any number of units. In other implementations, network environment 1300 may not have all of the components shown and/or may have other elements including other types of elements instead of, or in addition to, those shown herein.

In various implementations, each of units 1310, 1320, 1330, and 1340 may represent a sanitation system described herein. In some implementations, there may be multiple units at each entry point. For example, a particular entry point with double doors may have a unit for each door. As such, in this particular example, there may be two units at that entry point (e.g., one unit attached to each door).

In various implementations, users U1, U2, U3, and U4 may represent users interacting with respective units 1310, 1320, 1330, and 1340. For example, at one or more points in time, users U1, U2, U3, and U4 may interact with respective units 1310, 1320, 1330, and 1340 to pass through respective entry points.

Figure 14:
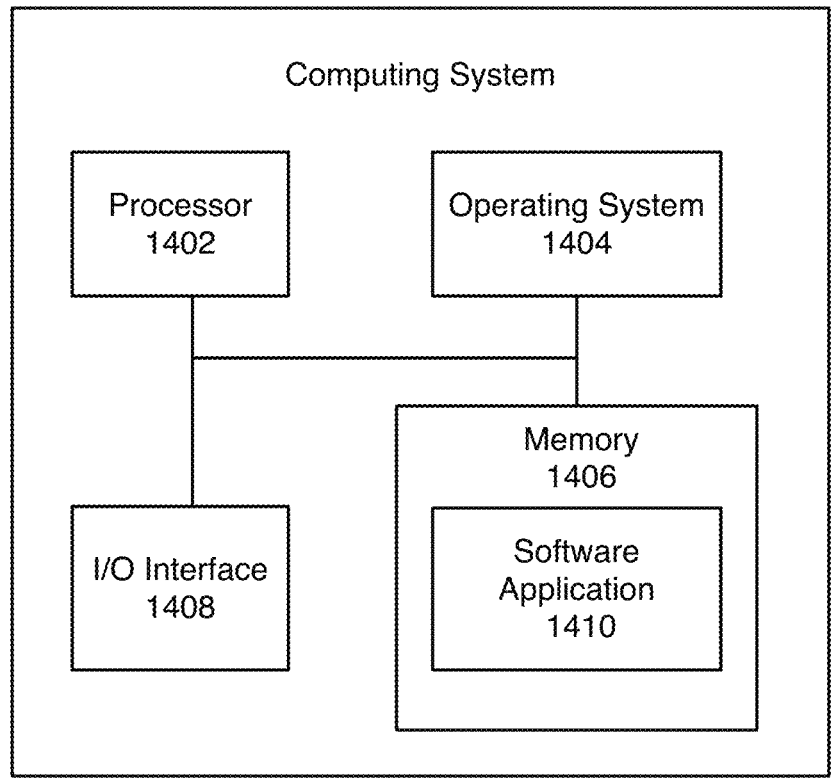
FIG. 14 illustrates a block diagram of an example computing device, which may be used for some implementations described herein.

FIG. 14 illustrates a block diagram of an example computing system 1400, which may be used for implementations described herein. For example, computing system 1400 may be used to implement server device 1304 of FIG. 13, as well as to perform the method implementations described herein. In some implementations, computing system 1400 may include a processor 1402, an operating system 1404, a memory 1406, and an input/output (I/O) interface 1408. In various implementations, processor 1402 may be used to implement various functions and features described herein, as well as to perform the method implementations described herein. While processor 1402 is described as performing implementations described herein, any suitable component or combination of components of system 1400 or any suitable processor or processors associated with system 1400 or any suitable system may perform the steps described. Implementations described herein may be carried out on a user device, on a server, or a combination of both.

Computing system 1400 also includes a software application 1410, which may be stored on memory 1406 or on any other suitable storage location or computer-readable medium. Software application 1410 provides instructions that enable processor 1402 to perform the functions described herein and other functions. The components of computing system 1400 may be implemented by one or more processors or any combination of hardware devices, as well as any combination of hardware, software, firmware, etc.

For ease of illustration, FIG. 14 shows one block for each of processor 1402, operating system 1404, memory 1406, I/O interface 1408, and software application 1410. These blocks 1402, 1404, 1406, 1408, and 1410 may represent multiple processors, operating systems, memories, I/O interfaces, and software applications. In various implementations, computing system 1400 may not have all of the components shown and/or may have other elements including other types of components instead of, or in addition to, those shown herein.

Although the description has been described with respect to particular embodiments thereof, these particular embodiments are merely illustrative, and not restrictive. Concepts illustrated in the examples may be applied to other examples and implementations.

Any suitable programming language may be used to implement the routines of particular embodiments including C, C++, Java, assembly language, and other program languages. Different programming techniques may be employed such as procedural or object-oriented. The routines may execute on a single processing device or on multiple processors. Although the steps, operations, or computations may be presented in a specific order, the order may be changed in particular embodiments. In some particular embodiments, multiple steps shown as sequential in this specification may be performed at the same time.

Particular embodiments may be implemented in a non-transitory computer-readable storage medium (also referred to as a machine-readable storage medium) for use by or in connection with an instruction execution system, apparatus, system, or device. Particular embodiments may be implemented in the form of control logic in software or hardware or a combination of both. The control logic, when executed by one or more processors, may be operable to perform that which is described in particular embodiments. For example, a tangible medium such as a hardware storage device can be used to store the control logic, which can include executable instructions.

A "processor" includes any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real time," "offline," in a "batch mode," etc. Portions of processing may be performed at different times and at different locations, by different (or the same) processing systems. A computer may be any processor in communication with a memory. The memory may be any suitable processor-readable storage medium, such as random-access memory (RAM), read-only memory (ROM), magnetic or optical disk, or other tangible media suitable for storing instructions (e.g., program or software instructions) for execution by the processor.

Particular embodiments may be implemented by using a programmed general purpose digital computer, and/or by using application specific integrated circuits, programmable logic devices, field programmable gate arrays, optical, chemical, biological, quantum or nanoengineered systems, components and mechanisms. In general, the functions of particular embodiments may be achieved by any means known in the art. Distributed, networked systems, components, and/or circuits may be used. Communication or transfer of data may be wired, wireless, or by any other means.

It will also be appreciated that one or more of the elements depicted in the drawings/figures may also be implemented in a more separated or integrated manner, or even removed or rendered as inoperable in certain cases, as is useful in accordance with a particular application. It is also within the spirit and scope to implement a program or code that is stored in a machine-readable medium to permit a computer to perform any of the methods described above.

As used in the description herein and throughout the claims that follow, "a", "an", and "the" include plural references unless the context clearly dictates otherwise. Also, as used in the description herein and throughout the claims that follow, the meaning of "in" includes "in" and "on" unless the context clearly dictates otherwise.

While one or more implementations have been described by way of example and in terms of the specific embodiments, it is to be understood that the implementations are not limited to the disclosed embodiments. To the contrary, they are intended to cover various modifications and similar arrangements as would be apparent to those skilled in the art. Therefore, the scope of the appended claims should be accorded the broadest interpretation so as to encompass all such modifications and similar arrangements.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

What is claimed is:

1. A system for sanitizing, the system comprising:
    a base;

a first sanitizer mechanism coupled to the base, wherein the first sanitizer mechanism is configured to sanitize at least one hand of a user;

a second sanitizer mechanism coupled to the base, wherein the second sanitizer mechanism is configured to sanitize a door handle, and wherein the second sanitizer mechanism comprises a light source that provides light onto the door handle to sanitize the door handle; and a controller system coupled to the base, wherein the controller system collects sanitation compliance information associated with one or more of the first sanitizer mechanism and the second sanitizer mechanism.

2. The system of claim 1, wherein the first sanitizer mechanism sanitizes the at least one hand of the user by applying a hand sanitizer to the at least one hand of the user.

3. The system of claim 1, wherein the first sanitizer mechanism sanitizes the at least one hand of the user by applying a hand sanitizer to the at least one hand of the user, and wherein the hand sanitizer is a gel.

4. The system of claim 1, wherein the first sanitizer mechanism sanitizes the at least one hand of the user by applying a hand sanitizer to the at least one hand of the user, and wherein the hand sanitizer is a foam.

5. The system of claim 1, wherein the first sanitizer mechanism comprises a nozzle for applying a hand sanitizer to the at least one hand of the user, and wherein the nozzle is positioned on an exterior of the first sanitizer mechanism.

6. The system of claim 1, wherein the second sanitizer mechanism sanitizes the door handle by applying a surface sanitizer to the door handle.

7. The system of claim 1, wherein the second sanitizer mechanism further comprises:

at least one door that opens and closes between the door handle and the user, wherein the second sanitizer mechanism sanitizes the door handle with the light while the at least one door is closed, and wherein the at least one door being closed shields the light from the user while the second sanitizer mechanism is sanitizing the door handle.

8. A system for sanitizing, the system comprising:
a base that mounts onto a door;
a door handle coupled to the base, wherein the door handle enables a user to operate the door;
a first sanitizer mechanism coupled to the base, wherein the first sanitizer mechanism is configured to sanitize at least one hand of the user;
a second sanitizer mechanism coupled to the base, wherein the second sanitizer mechanism is configured to sanitize a door handle, and wherein the second sanitizer mechanism comprises a light source that provides light onto the door handle to sanitize the door handle; and
a controller system coupled to the base, wherein the controller system collects sanitation compliance information associated with one or more of the first sanitizer mechanism and the second sanitizer mechanism.

9. The system of claim 8, wherein the first sanitizer mechanism sanitizes the at least one hand of the user by applying a hand sanitizer to the at least one hand of the user.

10. The system of claim 8, wherein the first sanitizer mechanism sanitizes the at least one hand of the user by applying a hand sanitizer to the hand of the user, and wherein the hand sanitizer is a gel.

11. The system of claim 8, wherein the first sanitizer mechanism sanitizes the at least one hand of the user by applying a hand sanitizer to the hand of the user, and wherein the hand sanitizer is a foam.

12. The system of claim 8, wherein the first sanitizer mechanism sanitizes comprises a nozzle for applying a hand sanitizer to the at least one hand of the user.

13. The system of claim 8, wherein the second sanitizer mechanism sanitizes the door handle by applying a surface sanitizer to the door handle.

14. The system of claim 8, wherein the second sanitizer mechanism sanitizes the door handle by applying a surface sanitizer to the door handle, and wherein the surface sanitizer is the light.

15. A method for sanitizing, the method comprising:
detecting a hand of a user;
sanitizing the hand of the user using a first sanitizer mechanism;
determining that the hand of the user has released a door handle;
sanitizing the door handle using a second sanitizer mechanism, wherein the second sanitizer mechanism comprises a light source that provides light onto the door handle to sanitize the door handle; and
collecting sanitation compliance information using a controller system, wherein the collecting sanitation compliance information is associated with one or more of the first sanitizer mechanism and the second sanitizer mechanism.

16. The method of claim 15, wherein the sanitizing of the hand of the user comprises applying a hand sanitizer to the hand of the user using a first sanitizer mechanism.

17. The method of claim 15, wherein the first sanitizer mechanism sanitizes the at least one hand of the user by applying a hand sanitizer to the hand of the user, and wherein the hand sanitizer is a gel.

18. The method of claim 15, wherein the first sanitizer mechanism sanitizes the at least one hand of the user by applying a hand sanitizer to the hand of the user, and wherein the hand sanitizer is a foam.

19. The method of claim 15, wherein the determining that the hand of the user has released a door handle comprises no longer detecting the at least one hand of the user.

20. The method of claim 15, wherein the sanitizing of the door handle comprises applying a surface sanitizer to the door handle using a second sanitizer mechanism.

* * * * *